(12) United States Patent
Sato et al.

(10) Patent No.: US 8,004,560 B2
(45) Date of Patent: *Aug. 23, 2011

(54) ENDOSCOPE APPARATUS

(75) Inventors: Saichi Sato, Sagamihara (JP); Yuusuke Kuwa, Tokyo (JP)

(73) Assignee: Olympus Corporation, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 12/765,260

(22) Filed: Apr. 22, 2010

(65) Prior Publication Data

US 2010/0201795 A1 Aug. 12, 2010

Related U.S. Application Data

(63) Continuation of application No. PCT/JP2008/067824, filed on Oct. 1, 2008.

(30) Foreign Application Priority Data

Oct. 30, 2007 (JP) ................. P2007-281641

(51) Int. Cl.
*A61B 1/04* (2006.01)
*A62B 1/04* (2006.01)
(52) U.S. Cl. ......................... 348/65; 600/111
(58) Field of Classification Search .............. 348/45, 348/65; 345/660; 600/111, 118
See application file for complete search history.

(56) References Cited

U.S. PATENT DOCUMENTS

| 6,914,623 | B2 * | 7/2005 | Ogawa | 348/45 |
|---|---|---|---|---|
| 6,945,930 | B2 * | 9/2005 | Yokota | 600/118 |
| 7,282,025 | B2 * | 10/2007 | Abe | 600/118 |
| 7,507,201 | B2 * | 3/2009 | Rovegno | 600/111 |
| 7,671,888 | B2 | 3/2010 | Nogami et al. | |
| 7,710,438 | B2 | 5/2010 | Furuhashi et al. | |
| 2002/0191074 | A1 | 12/2002 | Ogawa | |
| 2004/0019255 | A1 | 1/2004 | Sakiyama | |
| 2006/0176321 | A1* | 8/2006 | Nakano et al. | 345/660 |
| 2006/0203087 | A1 | 9/2006 | Kawanishi et al. | |
| 2007/0053555 | A1 | 3/2007 | Ooi et al. | |
| 2007/0142705 | A1 | 6/2007 | Ohnishi et al. | |

(Continued)

FOREIGN PATENT DOCUMENTS

EP 1 700 560 A1 9/2006

(Continued)

OTHER PUBLICATIONS

English Language International Search Report dated Dec. 22, 2008 issued in parent Appln. No. PCT/JP2008/067824.

(Continued)

*Primary Examiner* — Gims S Philippe
(74) *Attorney, Agent, or Firm* — Holtz, Holtz, Goodman & Chick PC

(57) ABSTRACT

An endoscope apparatus includes: a video signal acquisition portion; a video signal processing portion that processes a video signal to generate a display video signal; a measurement processing portion that performs measurement; and a display portion that displays the display video signal. The video signal processing portion generates a first display video signal based on one image extracted from the video signal, and a second display video signal based on the one image and other image of the video signal. During a period regarding measurement, the display portion displays the first display video signal or the second display video signal along with at least one of operation-related information and measurement information. A position where at least one of the operation-related information and the measurement information is displayed is controlled according to the first display video signal or the second display video signal displayed by the display portion.

18 Claims, 22 Drawing Sheets

U.S. PATENT DOCUMENTS

| | | |
|---|---|---|
| 2008/0068454 A1 | 3/2008 | Hirakawa |
| 2008/0167528 A1 | 7/2008 | Segawa et al. |
| 2010/0128116 A1* | 5/2010 | Sato et al. ................. 348/65 |

FOREIGN PATENT DOCUMENTS

| | | |
|---|---|---|
| JP | 2001-075019 A | 3/2001 |
| JP | 2001-167272 A | 6/2001 |
| JP | 2005-348870 A | 12/2005 |
| JP | 2006-180934 A | 7/2006 |

OTHER PUBLICATIONS

Japanese Office Action dated Jan. 27, 2009 and English translation thereof issued in a counterpart Japanese Application No. 2008-549703.

Japanese Office Action dated May 14, 2009 and English translation thereof issued in a counterpart Japanese Application No. 2008-549703.

U.S. Appl. No. 12/695,412, entitled: "Endoscope Apparatus," filed Jan. 28, 2010, Inventor: S. Sato.

Extended European Search Report dated Sep. 20, 2010 (in English) in counterpart European Application No. 10005577.1.

Extended European Search Report dated Oct. 5, 2010 (in English) in counterpart European Application No. 08843737.1.

Extended European Search Report dated Sep. 20, 2010 (in English) issued in counterpart European Application No. 10005577.1.

U.S. Office Action dated Apr. 15, 2011 in related U.S. Appl. No. 12/695,412.

* cited by examiner

ENDOSCOPE APPARATUS

CROSS REFERENCE TO RELATED APPLICATIONS

This application is a continuation application based on a PCT Patent Application No. PCT/JP2008/067824, filed Oct. 1, 2008, whose priority is claimed on Japanese Patent Application No. 2007-281641, filed on Oct. 30, 2007. The contents of both the PCT Application and the Japanese Application are incorporated herein by reference.

BACKGROUND OF THE INVENTION

1. Field of the Invention

The present invention relates to an endoscope apparatus in which a plurality of optical systems can be mounted.

2. Description of Related Art

Industrial endoscopes are used to observe or inspect inside damage, corrosion, and the like of a boiler, a turbine, an engine, a chemical plant, a water pipe, and the like. Industrial endoscopes have a plurality of kinds of optical adapters prepared to observe and inspect various objects, and tip portions of the endoscopes can be replaced.

An example of such an optical adapter includes an optical adapter for stereo measurement which forms two left and right fields of view in an observation optical system. Japanese Unexamined Patent Publication, First Publication No. 2005-348870 discloses an endoscope apparatus that uses an optical adapter for stereo measurement, calculates three-dimensional spatial coordinates of a subject on the basis of the coordinates of left and right optical system distance calculating points when a subject image is captured by left and right optical systems with parallax using the principle of triangulation, and performs three-dimensional measurement (stereo measurement) of the subject.

BRIEF DESCRIPTION OF THE INVENTION

According to an aspect of the present invention, an endoscope apparatus includes: a video signal acquisition portion that images a test subject by a stereo optical system to acquire a video signal; a video signal processing portion that processes the video signal to generate a display video signal; a measurement processing portion that performs measurement on the basis of the video signal; and a display portion that displays the display video signal, in which: the video signal processing portion generates a first display video signal based on one image extracted from the video signal including a plurality of images from the stereo optical system, and a second display video signal based on the one image and other image of the video signal; during a period regarding measurement, the display portion displays the first display video signal or the second display video signal along with at least one of operation-related information and measurement information; and a position where at least one of the operation-related information and the measurement information is displayed is controlled according to the first display video signal or the second display video signal displayed by the display portion.

DETAILED DESCRIPTION OF THE INVENTION

Figure 1:
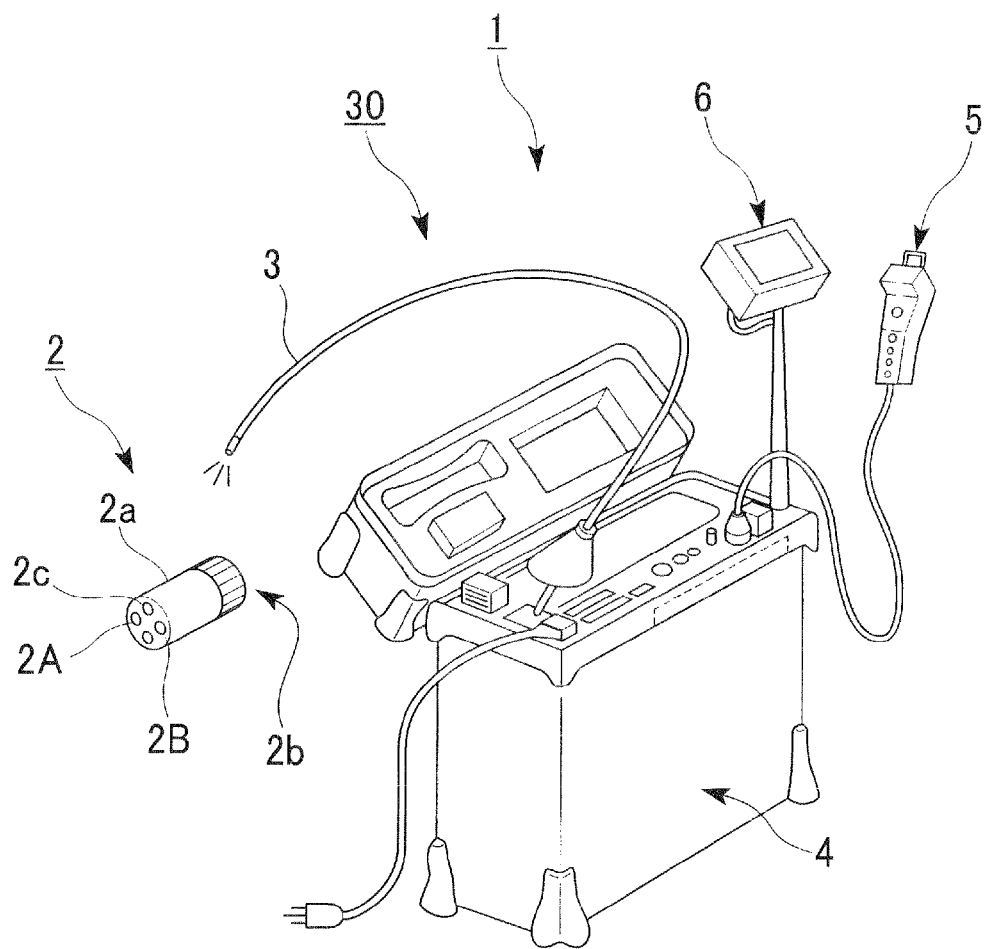
FIG. 1 is a perspective view of an endoscope apparatus according to an embodiment of the present invention.

Hereinafter, embodiments of the present invention will be described in detail. In the following embodiments, the same constituent components are denoted by the same reference numerals. In addition, a repeated explanation thereof will be omitted.

First, the structure and basic operation of an endoscope apparatus will be described. Next, among operations of the endoscope apparatus, an operation of measurement processing will be described in first and second embodiments and operations of image information recording processing and image file play processing will be described in third and fourth embodiments. The measurement processing, and the image information recording processing and the image file play processing may be separately performed. Therefore, the first and second embodiments, and the third and fourth embodiments may be combined arbitrarily.

Figure 2:
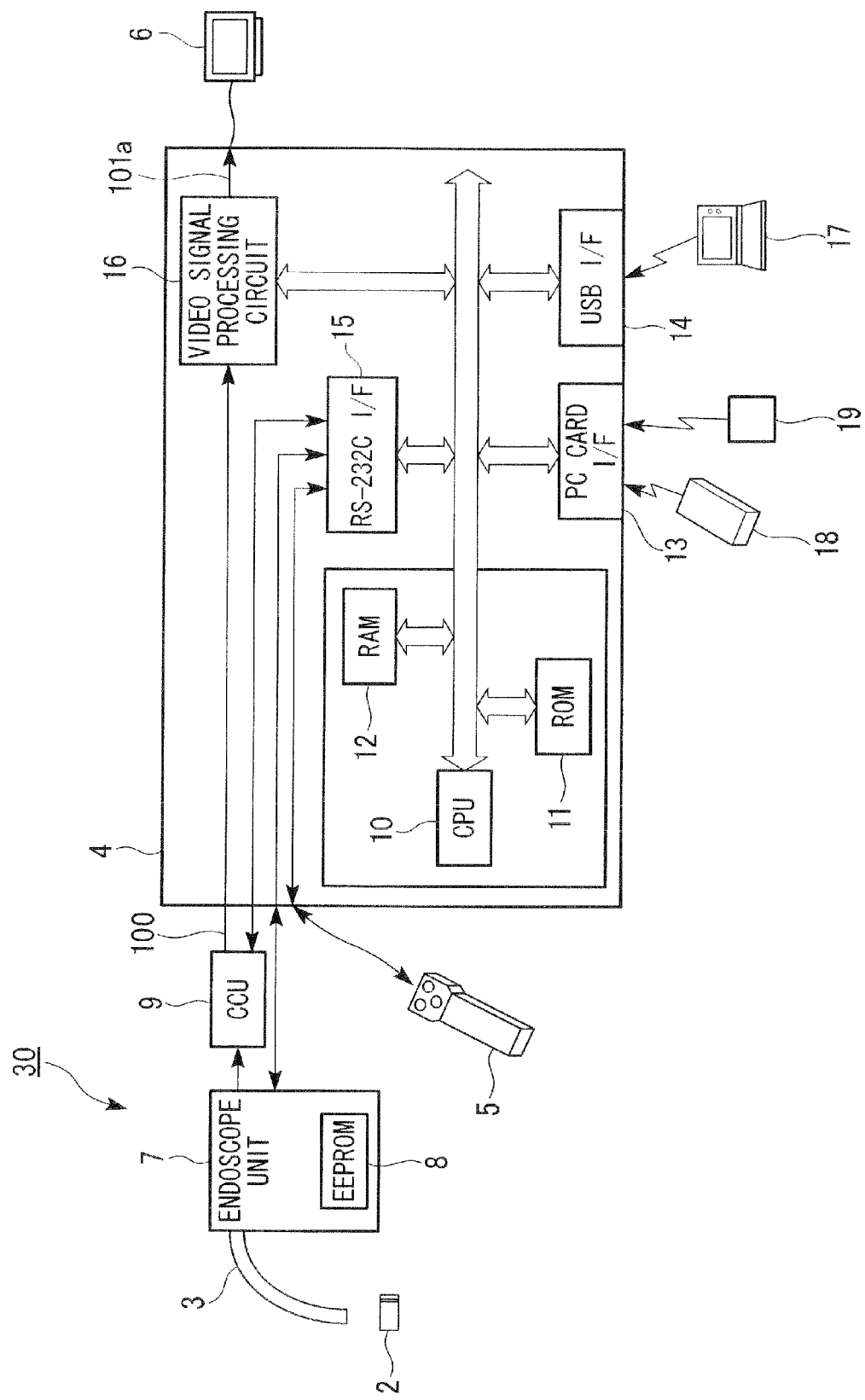
FIG. 2 is a block diagram showing the functional configuration of the endoscope apparatus according to the embodiment of the present invention.
Figure 3:
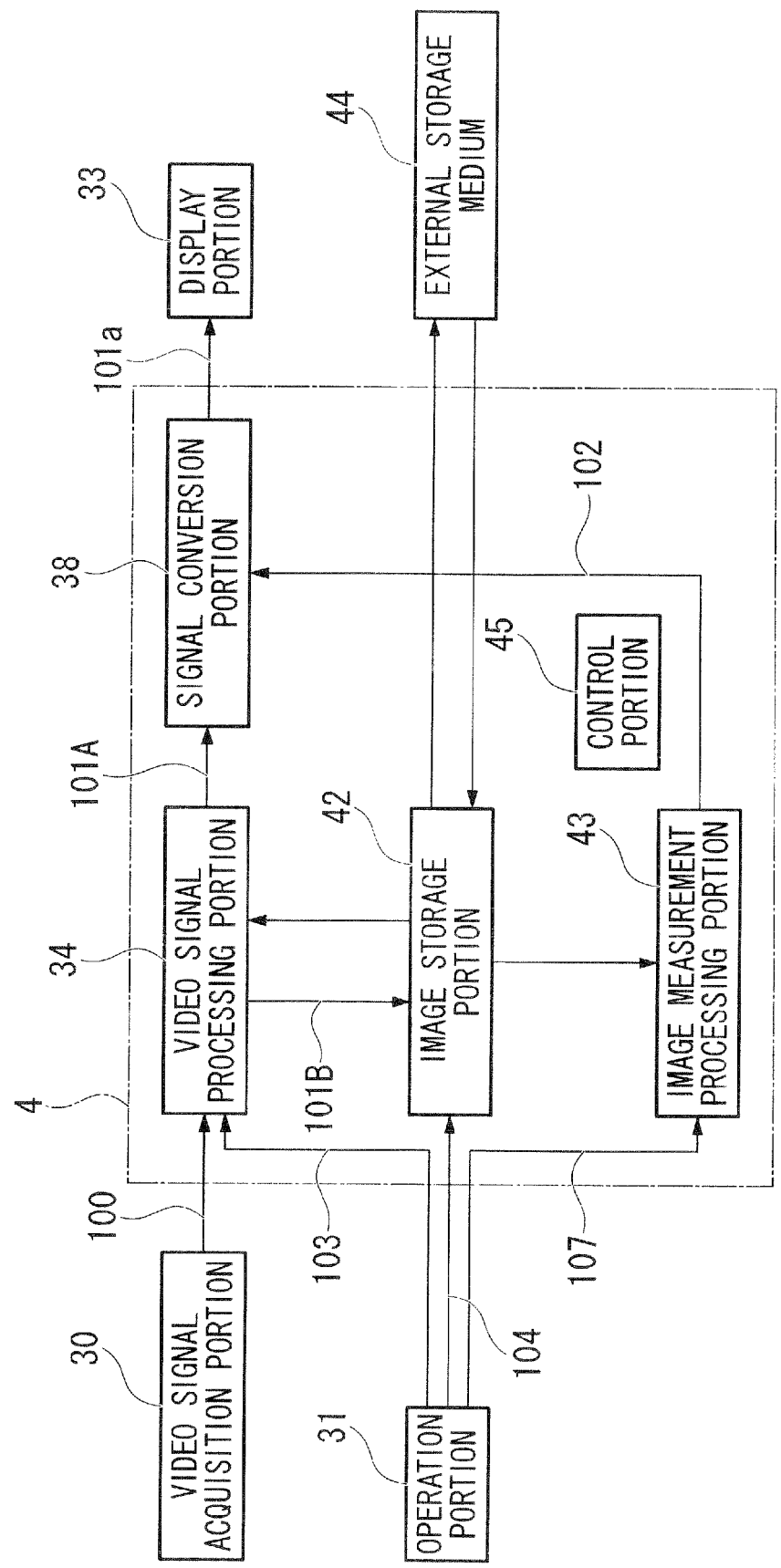
FIG. 3 is a block diagram showing the configuration of a control unit provided in the endoscope apparatus according to the embodiment of the present invention.

Hereinafter, the structure of the endoscope apparatus of an embodiment of the present invention will be described with reference to the drawings. FIG. 1 shows the appearance of a measuring endoscope apparatus of an embodiment of the present invention. FIG. 2 shows the functional configuration of the measuring endoscope apparatus of an embodiment of the present invention. FIG. 3 shows the functional configuration of a control unit provided in the measuring endoscope apparatus of an embodiment of the present invention.

A measuring endoscope apparatus 1 of an embodiment of the present invention images an object and measures a geometric characteristic of the object from the image. An examiner may appropriately replace an optical adapter on the tip of an endoscope insertion portion, appropriately select a built-in measurement processing program, or appropriately add a measurement processing program in order to perform various kinds of observation and measurement. Hereinbelow, a case where stereo measurement is performed as an example of measurement will be described.

As shown in FIGS. 1 and 2, the measuring endoscope apparatus 1 is configured to include an optical adapter 2 for stereo measurement, an endoscope insertion portion 3, an endoscope unit 7, a CCU 9 (camera control unit), a liquid crystal monitor 6 (display portion), a remote controller 5, and a control unit 4.

In the optical adapter 2 for stereo measurement, object lenses 2A and 2B, which are disposed to be spaced apart from each other by a predetermined distance in order to acquire images with parallax, are disposed within an adaptor body 2a having an approximately cylindrical shape. The optical adapter 2 for stereo measurement has a mounting portion 2b formed with a female screw and is detachably mounted on the tip of the endoscope insertion portion 3 using the mounting portion 2b.

The positions of the object lenses 2A and 2B are different depending on a direct view type that has a field of view at a tip surface of the optical adapter 2 for stereo measurement in the axial direction thereof or a side view type that has a field of view at a side surface of the optical adapter 2 for stereo measurement. In the present invention, the direct view type is shown. Accordingly, the object lenses 2A and 2B are disposed near an incidence opening provided on the tip surface of the optical adapter 2 for stereo measurement with optical axes thereof along the axis direction of the optical adapter 2 for stereo measurement. Moreover, an illumination window 2c that causes illumination light guided through the adaptor body 2a to be emitted toward an object is provided on the tip surface of the optical adapter 2 for stereo measurement. Note that, although the present invention is described using a stereo optical system having a dual lens, the same effects as in the present invention are also obtained in an optical system that acquires a stereo image, such as a prism. In addition, although the stereo optical system is provided in the optical adapter in the present invention, the stereo optical system may be provided in a tip portion of the endoscope insertion portion 3.

The endoscope insertion portion 3 is inserted into the inside of the object to image a region to be measured and then transmits an image signal to the control unit 4. A tip portion of the endoscope insertion portion 3 is formed so as to be capable of bending, and a mounting portion common to a plurality of optical adapters, such as the optical adapter 2 for stereo measurement, is provided in the tip portion so that each of the optical adapters can be mounted. Although not shown particularly, an imaging device, such as a CCD, which images an image formed by the plurality of object lenses of the optical adapter, and a light guide that causes illumination light to be illuminated on an object are provided inside the tip portion.

The endoscope insertion portion 3 has a long and narrow tube shape which is flexible over a range from the tip portion to a base portion thereof. A signal line of the imaging device, a light guide body, and a wire mechanism used to operate the tip portion to be bent (all of which are not shown) are disposed inside the endoscope insertion portion 3. In the case when the optical adapter 2 for stereo measurement is mounted in the endoscope insertion portion 3, a pair of images with parallax (hereinafter, referred to as 'parallax images') are acquired by the imaging device. Then, an image signal is transmitted to the CCU 9 through the signal line in the endoscope insertion portion 3.

The endoscope unit 7 is configured to include an illumination light source that generates illumination light guided to the light guide of the endoscope insertion portion 3, an electrically-operated bending driving unit for a wire mechanism, and an EEPROM 8 for storing a control parameter used to drive the electrically-operated bending driving unit. The endoscope unit 7 is connected to the distal end of the endoscope insertion portion 3 and is built in the control unit 4.

The CCU 9 controls imaging with the imaging device provided in the endoscope insertion portion 3 and converts an image signal acquired from the imaging device into a video signal, such as an NTSC signal. Then, the video signal is output as an input video signal 100 (refer to FIG. 3) to the control unit 4. Thus, the optical adapter 2 for stereo measurement, the endoscope insertion portion 3, the endoscope unit 7, and the CCU 9 form an endoscope including an optical adapter for stereo measurement and constitute a video signal acquisition portion 30 (refer to FIG. 3) that acquires parallax images.

The liquid crystal monitor 6 displays an image of an object and other information on the basis of a display video signal 101a (refer to FIG. 3) output from the control unit 4. The liquid crystal monitor 6 constitutes a display portion 33 (refer to FIG. 3). The image and information are displayed independently or together as needed. In case of performing stereo measurement like the present invention, the display video signal 101a includes one or both parallax images.

Other information includes, for example, operation input information from an operation portion, such as the remote controller 5 to be described later, an operation menu, and a graphical user interface (GUI) for operation (hereinafter, these operation-related information items are collectively referred to as an 'operation screen image data'). In addition, display of a cursor image used at the time of measurement and measurement information 102 (refer to FIG. 3) indicating a measurement result or the like are included.

The remote controller 5 is an operation portion for performing an operation input of the measuring endoscope apparatus 1 and is connected to the control unit 4. For example, ON and OFF of a power source, an operation related to calibration setting, an operation related to an imaging operation, an operation related to illumination, an operation related to driving for bending the endoscope insertion portion 3, an operation related to measurement, an operation of selecting the measurement accuracy at the time of measurement, an operation of selecting image processing for an image displayed on the liquid crystal monitor 6, an operation of recording image data in a storage medium or the like, an operation of reading image data recorded in a storage medium or the like, and the like may be mentioned as operation inputs performed by the remote controller 5. These operation inputs may be suitably performed through a user interface.

For example, although not shown particularly, a joystick, a lever switch, a freeze switch, a store switch, a measurement execution switch, and the like are provided in the remote controller 5. With these things, the examiner can perform various input operations by directly performing operation and instruction inputs of the measuring endoscope apparatus 1, performing a selective input of the operation menu, or operating the GUI displayed on the liquid crystal monitor 6. That is, the remote controller 5 has a function of an operation portion 31 (refer to FIG. 3) with which an examiner performs an operation input, such as measurement.

The control unit 4 controls operations of the measuring endoscope apparatus 1 including image processing on captured image data and calculation processing for image measurement. In the present invention, as shown in FIG. 2, the control unit 4 is configured to include a CPU 10, a ROM 11, a RAM 12, various input/output interfaces, and a video signal processing circuit 16, as hardwares.

The CPU 10 loads a control program, which has been stored in the ROM 11 or a storage medium 44 (refer to FIG. 3) to be described later, to the RAM 12, and executes the control program, thereby performing an operation corresponding to each function to be described later. For example, the control unit 4 includes an RS-232C interface 15, a PC card interface 13, and a USB interface 14, as input/output interfaces.

The RS-232C interface 15 performs communication for making an operation control between the remote controller 5, the endoscope unit 7, and the CCU 9. A PC card compliant with PCMCIA is connected to the PC card interface 13. In the present invention, a removable storage medium is mainly connected to the PC card interface 13, and the PC card interface 13 is used to load a program for operating the apparatus and store information on setting required for measurement, information on a measurement result, or image information. For this reason, various memory cards using a flash memory as a storage medium, for example, a PCMCIA memory card 18 and a compact flash (registered trademark) memory card 19 are mounted in the PC card interface 13.

A USB device is connected to the USB interface 14. In the present invention, a personal computer 17 is detachably connected to the USB interface 14. In addition, when the personal computer 17 is connected to the USB interface 4, communication is performed to transmit or receive various kinds of information stored in a storage medium or various kinds of information stored in a storage medium connected to the PC card interface 13 to or from a storage device or an internal memory of the personal computer 17, to play the information on a display monitor of the personal computer 17, or to perform various operation inputs with respect to the control unit 4 instead of the remote controller 5.

For this reason, when the personal computer 17 is connected to the USB interface 14, the personal computer 17 can also function as the liquid crystal monitor 6 connected to the control unit 4, the remote controller 5, and the storage medium. Accordingly, for example, a control related to measurement, image processing, image display, or the like can be performed using resources of the personal computer 17 as needed. That is, in this case, the personal computer 17 has functions of the operation portion 31 and display portion 33 in FIG. 3.

The video signal processing circuit 16 generates output video signals 101A and 101B by performing image processing, which is designated by the remote controller 5, on the input video signal 100 (refer to FIG. 3) supplied from the CCU 9. In addition, the video signal processing circuit 16 synthesizes the output video signals 101A and 101B with the operation screen image data or the measurement information 102 generated by the CPU 10, as needed, performs conversion into a signal such as an NTSC signal in order to display on the liquid crystal monitor 6, and outputs it to the liquid crystal monitor 6 as the display video signal 101a.

Next, the stereo measurement performed by the measuring endoscope apparatus 1 will be described. In the stereo measurement performed by the measuring endoscope apparatus 1, at least the following first to sixth processings are performed. The first processing is processing for reading optical information from a storage medium in which optical data of the optical adapter 2 for stereo measurement has been recorded. The second processing is processing for reading positional relationship information between an imaging device disposed within the tip portion of the endoscope insertion portion 3 and an object lens system of the optical adapter 2 for stereo measurement.

The third processing is processing for calculating a positional error of the imaging device of the measuring endoscope apparatus 1 from the above-described positional relationship information, and positional relationship information between an imaging device of an endoscope used as the reference and the object lens system of the optical adapter 2 for stereo measurement, which was obtained at the time of production. The fourth processing is processing for correcting optical data based on the positional error. The fifth processing is processing for performing coordinate transformation of an image to be measured on the basis of the corrected optical data. The sixth processing is processing for calculating three-dimensional coordinates of an arbitrary point by matching two images on the basis of the image for which the coordinate transformation was performed.

For example, the CPU 10 makes a control such that the first to fourth processings are performed once for the optical adapter 2 for stereo measurement and the result is recorded as measuring environment data in the storage medium. The first to fourth processings are collectively called calibration processing. Thereafter, when performing the stereo measurement, the CPU 10 makes a control such that the measuring environment data is loaded to the RAM 12 to perform the fifth and sixth processings.

Note that, when performing the second processing for reading the positional relationship information between the imaging device in the tip portion and the object lens system of the optical adapter 2 for stereo measurement, the CPU 10 performs the second processing by acquiring the shape of a mask provided in the optical adapter 2 for stereo measurement and comparing the shape and position of the mask at the time of production. In this case, acquisition of the mask shape is performed by imaging an object for calibration and obtaining a white image.

Next, referring to FIG. 3, a function of the control unit 4 will be described focusing on each functional block relevant to the video signal processing circuit 16. The functional block of the control unit 4 is configured to include a video signal processing portion 34, a signal conversion portion 38, an image storage portion 42, an image measurement processing portion 43, and a control portion 45. Here, the video signal processing portion 34 and the signal conversion portion 38 are formed by the video signal processing circuit 16 shown in FIG. 2.

From the video signal acquisition portion 30 configured to include the optical adapter 2 for stereo measurement, the endoscope insertion portion 3, the endoscope unit 7, and the CCU 9, one-frame image information including a pair of parallax images on which preprocessing, such as brightness level adjustment or noise removal processing, was performed by the CCU 9 is input to the video signal processing portion 34 as the input video signal 100. The preprocessing may be performed as image processing by the video signal processing portion 34.

The video signal processing portion 34 performs image processing on the input video signal 100 to generate the output video signal 101A and outputs it to the signal conversion portion 38. In addition, the video signal processing portion 34 can generate the output video signal 101B and output it to the image storage portion 42. Note that the output video signals 101A and 101B may be not only different signals but also the same signals on which the same image processing is performed.

The signal conversion portion 38 outputs the output video signal 101A, which was output from the video signal processing portion 34, to the display portion 33 as the display video signal 101*a*. In this case, other image data such as the operation screen image data may be synthesized in the display video signal 101*a*, as needed. Moreover, when the measurement information 102 is output from the image measurement processing portion 43, the signal conversion portion 38 may generate the display video signal 101*a* in a state where the measurement information 102 is also synthesized.

A measurement start/end signal 103 from the operation portion 31 is also input to the video signal processing portion 34.

When receiving signals of measurement start and measurement end from the operation portion 31, the video signal processing portion 34 outputs the input video signal 100 from the video signal acquisition portion 30, as the output video signal 101A, to the signal conversion portion 38.

The image storage portion 42 serves to store the output video signal 101B, which is output from the video signal processing portion 34, as still image data, and is provided on the RAM 12. Moreover, when an image recording signal 104 is input from the operation portion 31, the still image data is read from the image storage portion 42 according to control of the control portion 45. Then, the still image data is output to the storage medium 44 and is stored in the storage medium 44.

The image measurement processing portion 43 performs measurement processing using the still image data stored in the image storage portion 42 and generates measurement GUI image data required for a measurement operation input. In the present invention, the image measurement processing portion 43 performs stereo measurement using a known algorithm. For example, when a measuring point is input on a display image of the liquid crystal monitor 6 by the operation portion 31, the image measurement processing portion 43 acquires information on the position of a corresponding point on each parallax image corresponding to the measuring point by matching processing based on each brightness information item. In addition, the image measurement processing portion 43 calculates the three-dimensional coordinates of the measuring point by the principle of triangulation.

For example, measurement input information 107, which is input to the image measurement processing portion 43 and is acquired through a GUI that allows a positioning cursor on the liquid crystal monitor 6 to operate by the remote controller 5 or the like, is used as the information of a measuring point. A measurement result of the stereo measurement is output to the signal conversion portion 38, as the measurement information 102, together with the measurement GUI image data including a measured distance, a mark of a measuring point, and the like, is synthesized with an image of the output video signal 101A in the signal conversion portion 38, and is displayed on the display portion 33.

The control portion 45 is configured to include the CPU 10, the ROM 11, and the RAM 12. The control portion 45 controls an operation of each portion by making the CPU 10 read a control program stored in the ROM 11 and loading the control program to the RAM 12 and the CPU 10 execute a command described in the control program. Note that, in FIG. 3, an arrow that connects the control portion 45 with each portion is omitted to avoid the drawing becoming complicated.

Next, a basic operation of the measuring endoscope apparatus 1 will be described. Before starting the measurement, optical characteristic information on the optical adapter 2 for stereo measurement, for example, magnification information or distortion characteristic information on a lens, is set. This may be input by the examiner by using the remote controller 5 or reading a condition stored in the storage medium. This optical characteristic information is stored in the RAM 12. The examiner inserts the endoscope insertion portion 3 mounted with the optical adapter 2 for stereo measurement into an object and moves the endoscope insertion portion 3 toward a desired measurement position of the object by adjusting bending of the tip portion by the remote controller 5.

An image, which is formed on the imaging device through the optical adapter 2 for stereo measurement, is output as the input video signal 100 to the control unit 4 through the CCU 9. Then, the image of the object is displayed on the liquid crystal monitor 6. The examiner sets a measuring position of the object while observing the image. Then, the positioning cursor for setting the measuring point is displayed on the liquid crystal monitor 6. For example, in the case of performing distance measurement, the examiner designates two measuring points. Then, the examiner performs an operation input which is to press a measurement start switch from the operation portion 31 of the remote controller 5, for example. Then, the operation portion 31 outputs the measurement start signal 103 to the video signal processing portion 34 and the measurement input information 107 to the image measurement processing portion 43.

The output video signal 101A which has been subjected to image processing by the video signal processing portion 34 is output to the signal conversion portion 38. In addition, the output video signal 101B from the video signal processing portion 34 is stored as still image data in the image storage portion 42. Here, the output video signal 101B may be the same video signal as the input video signal 100 or may be one obtained by performing image processing (edge correction or the like), which does not affect the measurement accuracy, on the input video signal 100.

When the output video signal 101B is stored in the image storage portion 42, the image measurement processing portion 43 starts an image measurement calculation on the basis of the measurement input information 107. Then, the measurement result is output as the measurement information 102 to the signal conversion portion 38. The signal conversion portion 38 generates the display video signal 101a, which is obtained by synthesizing the measurement information 102 with the output video signal 101A, and outputs it to the liquid crystal monitor 6. Thus, an image of the display video signal 101a is displayed on the liquid crystal monitor 6.

Figure 4:
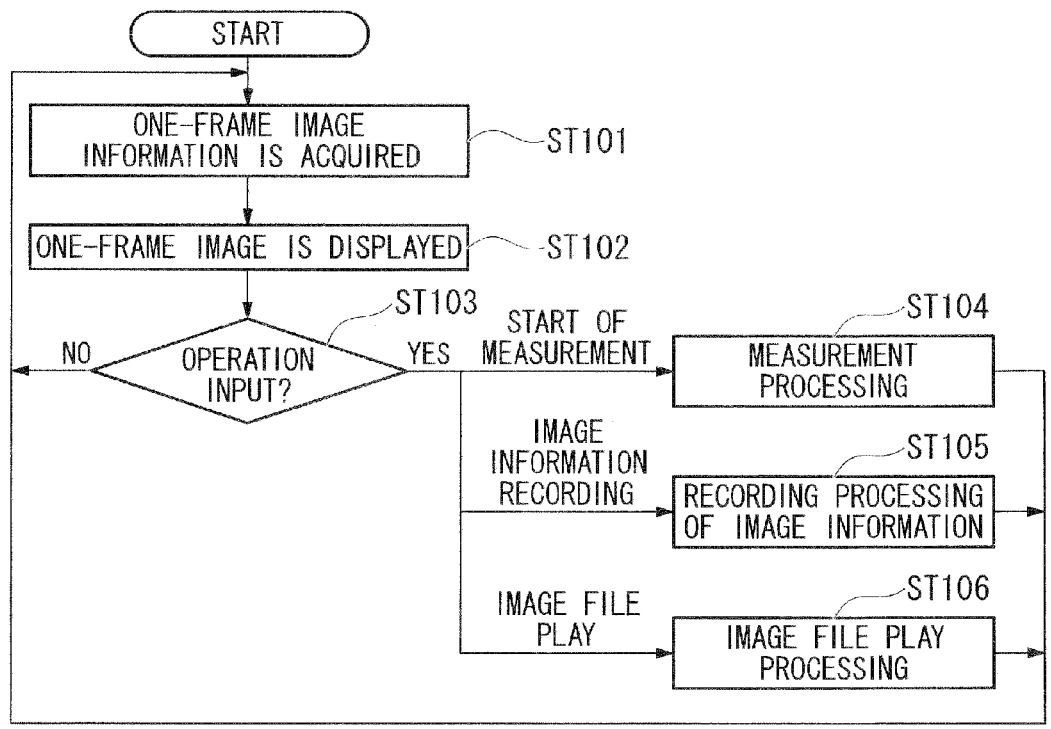
FIG. 4 is a flow chart showing the procedure of an operation (entire processing) of the endoscope apparatus according to the embodiment of the present invention.

Next, a measurement operation of the measuring endoscope apparatus 1 will be described while referring to flow charts and examples of a display screen. FIG. 4 shows the procedure of the entire operation of the measuring endoscope apparatus 1. When power is supplied, the measuring endoscope apparatus 1 operates in an image display mode in which an image acquired through the optical adapter 2 for stereo measurement is displayed on the liquid crystal monitor 6. Moreover, the measuring endoscope apparatus 1 operates in various processing modes corresponding to operation inputs when an operation input occurs from the operation portion, such as the remote controller 5. Hereinafter, modes in which measurement processing, image information recording processing, and image file play processing are performed will be described as examples of various processing modes.

First, as shown in FIG. 4, in ST101, the video signal acquisition portion 30 acquires image information corresponding to one frame. That is, the input video signal 100 is output from the video signal acquisition portion 30 to the video signal processing portion 34 of the control unit 4, and the one-frame input video signal 100 is acquired as image information by the video signal processing portion 34.

Then, in ST102, the video signal processing portion 34 outputs the one-frame video signal of the input video signal 100, as the output video signal 101A, to the signal conversion portion 38 without any change. The signal conversion portion 38 outputs the display video signal 101a, in which other image data is synthesized, to the display portion 33. Thus, an image based on the video signal acquired by the video signal acquisition portion 30 is displayed on the display portion 33. After ST102 ends, the process proceeds to ST103.

In ST103, the control portion 45 checks whether or not an operation input has been performed. When the operation input has been performed, processing corresponding to the operation input is performed. For example, when the operation input for starting the measurement has been performed, the process proceeds to ST104. In addition, when an operation input for recording image information in an image file to be described later has been performed, the process proceeds to ST105. In addition, when an operation input for playing the image information recorded in the image file to be described later has been performed, the process proceeds to ST106. On the other hand, when an operation input is not performed, the process proceeds to ST101 in which image information corresponding to following one frame is acquired and those described above are repeated.

As a result, when an operation input does not occur, an image display mode in which an image for every one frame subjected to current image processing is displayed on the display portion 33 in an approximately real-time manner is realized.

Figure 5:
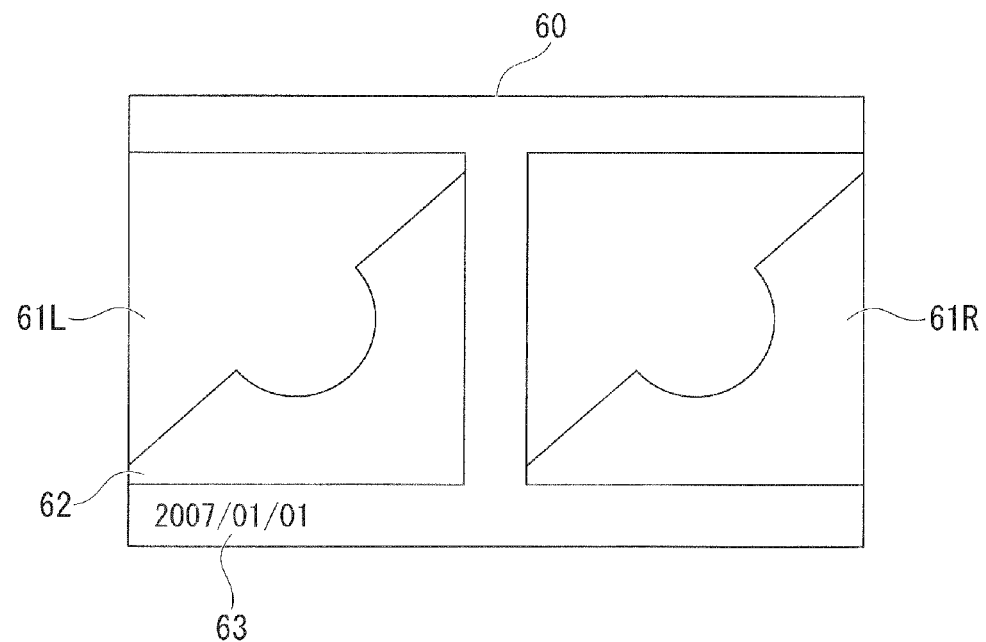
FIG. 5 is a reference view showing a display screen of the endoscope apparatus according to the embodiment of the present invention.

FIG. 5 shows an example of a display screen in the image display mode. In the image display mode, a display screen 60 includes an I-shaped display region, which includes upper, lower, and middle parts of a screen of the display portion 33, and two display regions with approximately rectangular shapes excluding the I-shaped display region. A parallax image 61L is displayed in the left approximately rectangular shaped display region shown in the drawing in an approximately real-time manner, and a parallax image 61R is displayed in the approximately rectangular shaped right display region shown in the drawing in an approximately real-time manner. The parallax images 61L and 61R are a pair of parallax images corresponding to a pair of images acquired at the same time through the object lenses 2B and 2A of the optical adapter 2 for stereo measurement, respectively.

In the example shown in FIG. 5, an object 62 (for example, a turbine blade) having a three-dimensional shape is displayed in a lower half portion of each parallax image. In addition to those described above, image information, text information, and the like may be appropriately displayed on the display screen 60. In the present invention, a current date is displayed as date information 63 in a bottom region of the parallax image 61L in a real-time manner.

First Embodiment

Figure 6:
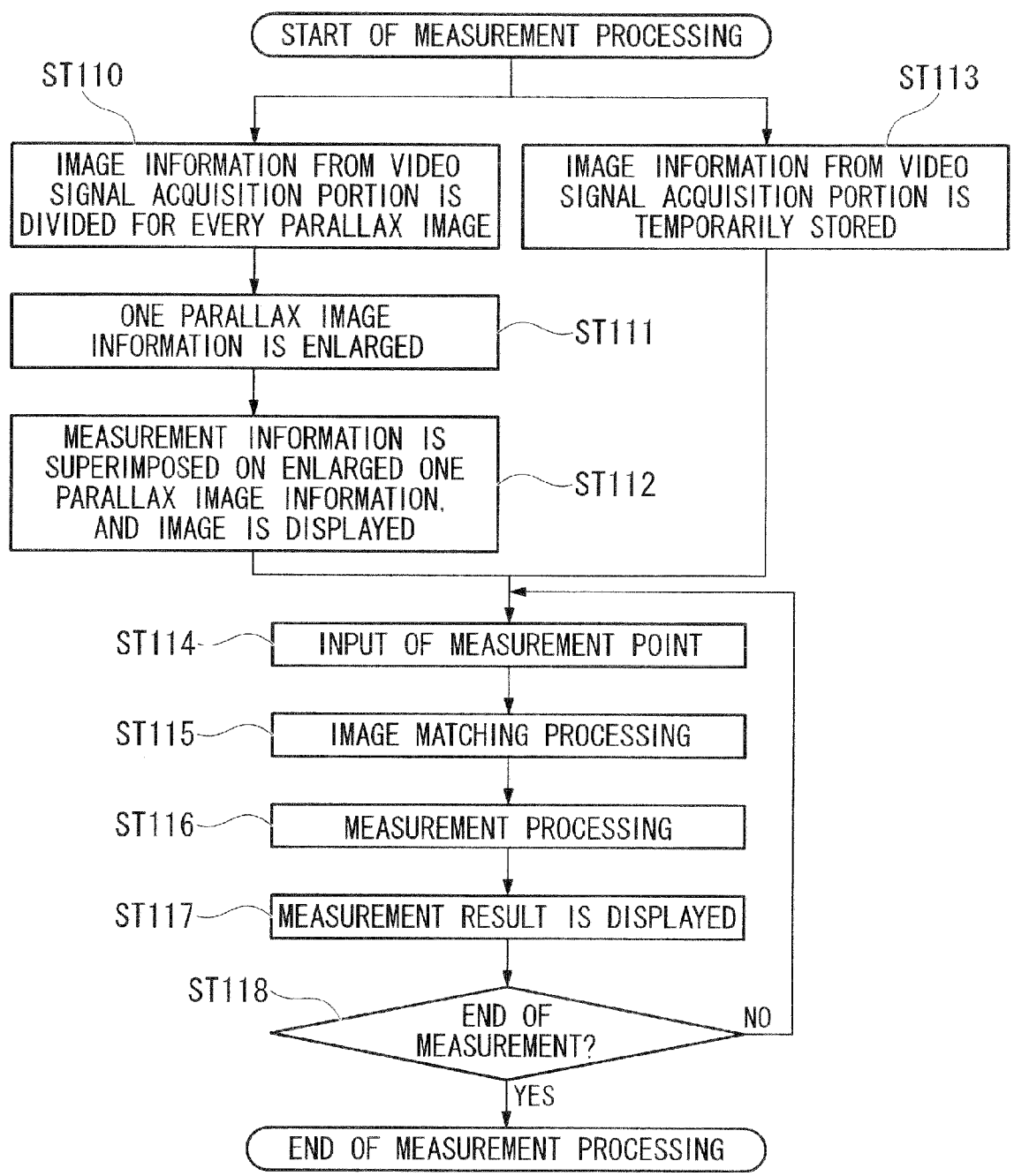
FIG. 6 is a flow chart showing the procedure of an operation (measurement processing) of the endoscope apparatus according to a first embodiment of the present invention.

Hereinafter, a first embodiment of the present invention will be described with reference to the drawings. The present embodiment relates to measurement processing, that is, an operation when an operation input for starting measurement is performed as the operation input in ST102 of FIG. 4. First, when an operation input for starting the measurement is performed as the operation input, that is, when the measurement start signal 103 is input from the operation portion 31, measurement processing shown in FIG. 6 is performed as ST104. However, the processing of ST110 to ST112 is a processing for generating the output video signal 101A and the processing of ST113 is a processing for generating the output video signal 101B, and the processing of ST110 to ST112 and the processing of ST113 are executed simultaneously and in parallel through two systems.

In ST110, the video signal processing portion 34 performs processing for dividing an image of the input video signal 100 from the video signal acquisition portion 30 into two images of the parallax images 61L and 61R of FIG. 5. That is, the video signal processing portion divides the acquired image information for every parallax image.

Then, in ST111, the video signal processing portion 34 performs processing for enlarging one parallax image (parallax image 61L) of the two parallax images divided in ST110. A video signal based on a parallax image 61La after enlarging processing is output as the output video signal 101A to the signal conversion portion 38. In the present embodiment, the video signal processing portion 34 performs enlarging processing on the entire parallax image 61L to set it as the parallax image 61La such that the length of the parallax image 61La after enlarging processing in the longitudinal direction is approximately equal to the length of the screen of the display portion 33 in the longitudinal direction.

Then, in ST112, the signal conversion portion 38 superimposes the measurement information 102, which is generated in the image measurement processing portion 43, on the output video signal 101A based on the parallax image 61La after enlarging processing and outputs it to the display portion 33 as the display video signal 101*a*. The display portion 33 displays the parallax image 61La after enlarging processing on the basis of the display video signal 101*a*. The visibility for the examiner can be raised by displaying one of the two parallax images 61L and 61R. In addition, the visibility can be further improved by enlarging the one parallax image and displaying it. Although the parallax image 61L is used in this example, the other parallax image 61R may alternatively be used.

ST113 is processed in parallel with the above-described ST110 to ST112. In ST113, the output video signal 101B is output from the video signal processing portion 34 to the image storage portion 42 and is temporarily stored in the image storage portion 42. The output video signal 101B is a video signal based on image data including both the parallax images 61L and 61R, similar to the input video signal 100. In the present embodiment, the stereo measurement processing performed by the image measurement processing portion 43 calculates the three-dimensional coordinates of a measuring point by the principle of triangulation. Accordingly, a measurement video signal 101*b* having both the left and right parallax images is temporarily stored in the image storage portion 42 separately from the display video signal 101*a*.

Figure 7:
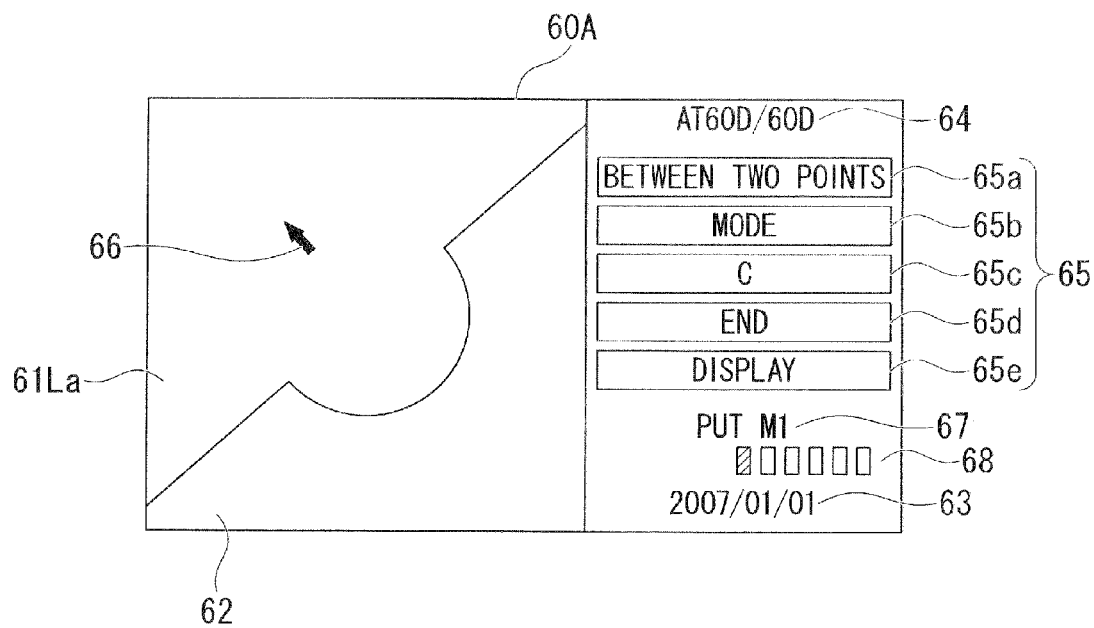
FIG. 7 is a reference view showing a display screen of the endoscope apparatus according to the first embodiment of the present invention.

FIG. 7 shows an example of a display screen 60A at the start of a measurement mode. In addition to the parallax image 61La after enlarging processing and the date information 63, measurement condition information 64 corresponding to the measurement GUI image data, an operation icon 65, a measurement cursor 66, message information 67, image matching degree information 68, and the like are displayed on the display screen 60A.

The display screen 60A is configured to include two approximately rectangular display regions disposed on the left and right sides. The left display region of the two display regions is similar to the display region of the display screen 60 shown in FIG. 5 where the parallax image 61L is displayed. However, the left display region is formed so as to enlarge the display region of the display screen 60 shown in FIG. 5 where the parallax image 61L is displayed such that the length thereof in the longitudinal direction is approximately equal to the length of the display portion 33 in the longitudinal direction. The parallax image 61La after enlarging processing is displayed in the left display region of the display screen 60A. The date information 63, the measurement condition information 64, the operation icon 65, the message information 67, the image matching degree information 68, and the like are displayed in the right display region of the display screen 60A. The measurement cursor 66 is displayed so as to overlap the parallax image 61La after enlarging processing.

Thus, in the present embodiment, the entire parallax image 61L is subjected to enlarging processing up to a region, in which the parallax images 61L and R were not displayed in the display screen 60 shown in FIG. 5, and is displayed as the parallax image 61La.

The measurement condition information 64 shows information on a current measurement condition. In the present embodiment, the type of the optical adapter 2 for stereo measurement being used is displayed as an example. As an example, the operation icon 65 includes: a measurement switching icon 65*a* for setting types of measurement operations to be performed, for example, a distance ('between two points'), a depth, an area, and an angle; a mode switching icon 65*b* for changes of various settings, such as a change of the shape or color of the measurement cursor 66; a clear icon 65*c* for clearing a measuring point, an execution result of measurement, and the like; a termination icon 65*d* for terminating measurement processing; and a display switching icon 65*e* for inputting an instruction for changing the display form of the display screen 60A to be described later.

The measurement cursor 66 is for inputting a measuring point on the display screen 60A in response to an operation input from the operation portion 31 or performs an operation such as selection of an icon or menu. The message information 67 displays information on the operation or measurement as various kinds of text information or numerical information. For example, in FIG. 7, operation guidance (example: PUT M1=input of a first measuring point) is displayed.

The image matching degree information 68 indicates the degree (hereinafter, referred to as matching degree) of matching between a designated position of one parallax image (in this example, the parallax image 61L) input by the examiner and the corresponding position of another parallax image (in this example, the parallax image 61R). This matching degree is calculated by the image measurement processing portion 43. The matching degree is expressed by six square indicators, and a smaller number of square indicators are displayed as the matching degree becomes stronger (as images at the designated position further match each other).

Moreover, object distance information may be displayed instead of the image matching degree information 68.

The object distance information shows the degree of the distance between the tip portion of the endoscope insertion portion 3 and the object 62. This object distance is calculated by the image measurement processing portion 43. The object distance is expressed by six square indicators, and a smaller number of square indicators are displayed as the object distance becomes smaller.

In addition, although the matching degree information or the object distance information is expressed by the square indicators in this example, they may be expressed by numeric values or in other forms.

As shown in FIG. 6, after the above-described ST112 and ST113 end, the process proceeds to ST114.

Figure 8:
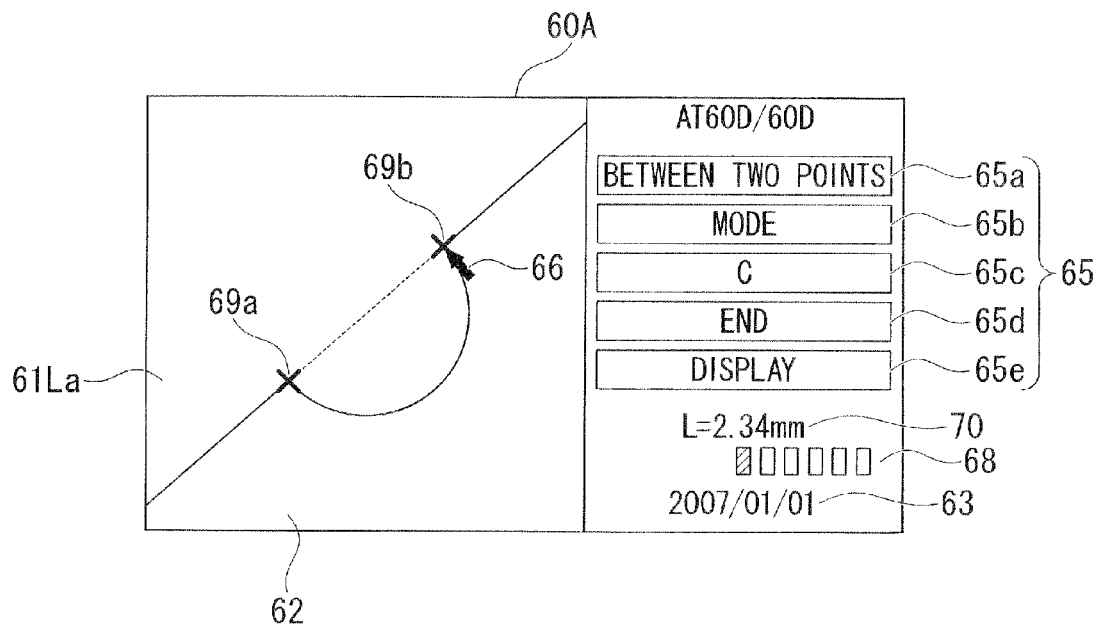
FIG. 8 is a reference view showing a display screen of the endoscope apparatus according to the first embodiment of the present invention.

In ST114, a message that requests a measuring point input is displayed as the message information 67 of FIG. 7, and the measuring point input is received. The examiner inputs a measuring point by moving the measurement cursor 66 and selecting a position on the screen with the operation portion 31 while observing the display screen 60A of the display portion 33. In addition, whenever the position is selected, coordinate information on the parallax image 61L (parallax image 61La after enlarging processing) is acquired and, for example, X-shaped selected position display FIGS. 69*a* and 69*b* are displayed so as to overlap the parallax image 61La after enlarging processing, as shown in FIG. 8. For example, in the case of distance measurement, ST114 ends when the examiner designates two positions as described above, and the process proceeds to ST115.

In ST115, the image measurement processing portion 43 reads the output video signal 101B, which is temporarily stored in the image storage portion 42 in ST113, from the image storage portion 42. Then, the image measurement processing portion 43 calculates a corresponding position on the parallax image 61R, which corresponds to the measuring position on the parallax image 61L input in ST114, by image matching processing on the basis of the still image data based on the read output video signal 101B.

In ST116, the image measurement processing portion 43 performs measurement processing using the parallax of two images on the basis of the measuring position on the parallax image 61L input in ST114 and the corresponding position on the parallax image 61R corresponding to the measuring position on the parallax image 61L calculated in ST115.

Then, in ST117, the image measurement processing portion 43 outputs a result of the measurement processing performed in ST116, as the measurement information 102, to the signal conversion portion 38. The signal conversion portion 38 superimposes the measurement information 102, which was generated in the image measurement processing portion 43, on the output video signal 101A from the video signal processing portion 34 and outputs it to the display portion 33 as the display video signal 101*a*. The display portion 33 displays the parallax image 61La after enlarging processing on the basis of the display video signal 101*a*. As a result, measurement result information 70 is displayed as shown in FIG. 8. As an example, in FIG. 8, a measurement distance L between two points (69*a*, 69*b*) is displayed as 'L=2.34 mm'

Then, in ST118, the control portion 45 checks whether or not an operation for terminating the measurement has been performed in the operation portion 31. When the operation for terminating the measurement has not been performed, the process proceeds to ST114. In addition, when the operation for terminating the measurement is performed, the measurement processing ends and the process proceeds to ST101 of FIG. 4. Then, the operation of the measuring endoscope apparatus 1 moves to the image display mode and an operation of acquiring image information of a next frame is performed.

Figure 29:
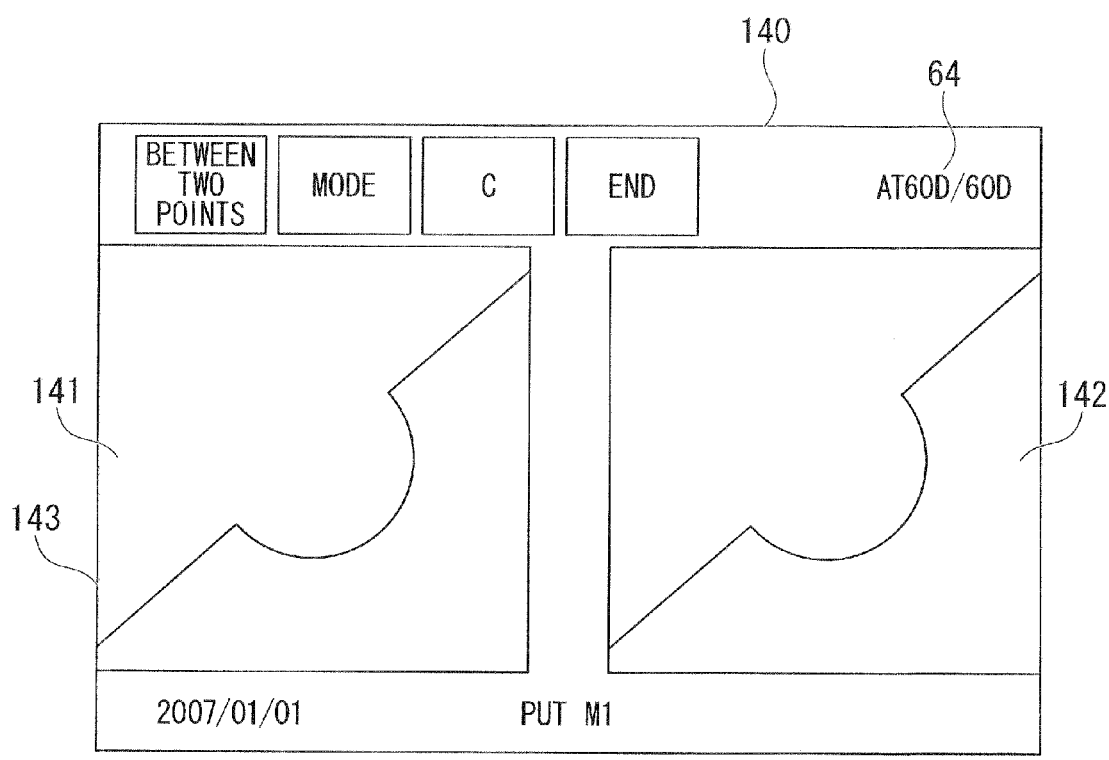
FIG. 29 is a reference view showing a display screen of a known endoscope apparatus.

As described above, in ST115 of FIG. 6, the matching degree of image between the position that the examiner designated on one parallax image (in this example, the parallax image 61L) and the position on the other parallax image (in this example, the parallax image 61R) is calculated, and the calculation result is displayed in ST117. At this time, the display screen 60A of FIG. 7, on which only the parallax image 61La after enlarging processing is displayed, and the display screen (display screen similar to the known display screen 140 shown in FIG. 29), on which both the parallax images 61L and 61R are displayed, may be switched to be displayed.

For example, when the examiner sees the image matching degree information 68 of FIG. 7 and selects the display switching icon 65*e*, the control portion 45 recognizes that a display screen switching instruction is input and executes processing for switching of a display screen. The video signal processing portion 34 outputs a video signal based on image data including both the parallax images 61L and 61R, as the output video signal 101A, to the signal conversion portion 38 on the basis of the instruction from the control portion 45. As a result, the screen returns to the display screen on which both the parallax images 61L and 61R are displayed. Then, the examiner can visually check whether or not the designated points on the parallax images 61L and 61R match.

Moreover, when the matching degree is low, a display screen on which both the parallax images 61L and 61R are displayed may be automatically displayed so that the examiner visually checks whether or not the designated points on the parallax images 61L and 61R match. In this case, the control portion 45 determines whether or not the matching degree is low by comparing the matching degree calculated by the image measurement processing portion 43 with a threshold value. The control portion 45 determines whether to switch the display screen according to the determination result. The threshold value used for comparison with the matching degree may be a fixed value or may be set by the examiner. When the matching degree is low, the control portion 45 executes processing for switching of a display screen. The video signal processing portion 34 outputs a video signal based on the image data including both the parallax images 61L and 61R, as the output video signal 101A, to the signal conversion portion 38 on the basis of the instruction from the control portion 45.

Figure 9:
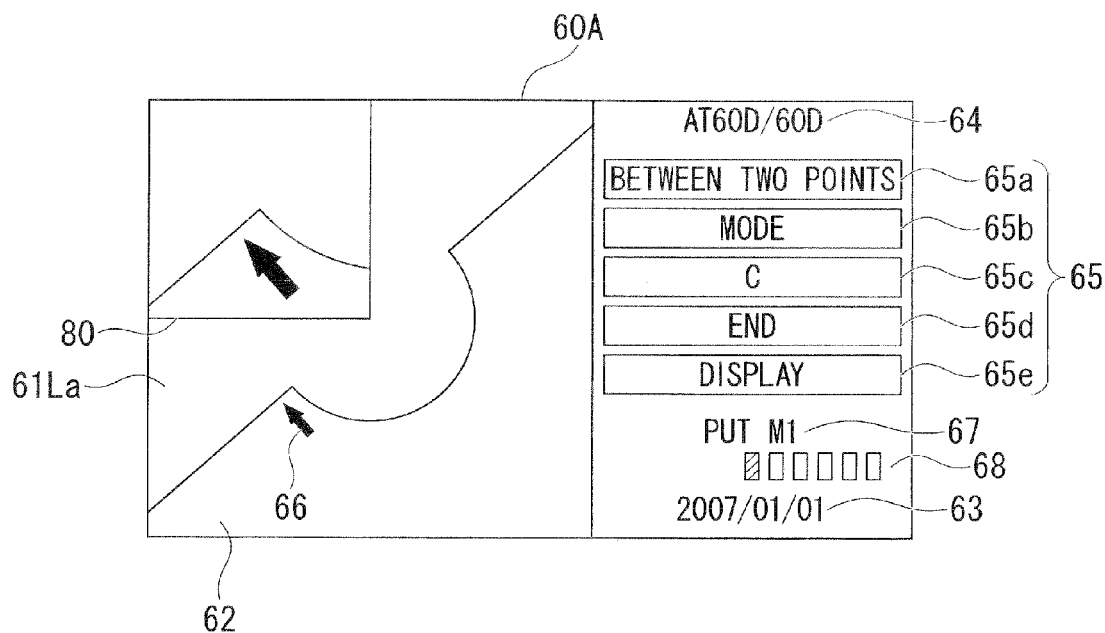
FIG. 9 is a reference view showing a display screen of the endoscope apparatus according to the first embodiment of the present invention.

Moreover, as shown in FIG. 9, in order to make the examiner visually check on the display screen 60A whether or not the designated points match between the parallax images, the control portion 45 may perform display by overlapping a peripheral image 80 obtained by extracting the periphery of the parallax image 61R at a position that the examiner designated on the parallax image 61L (parallax image 61La). Furthermore, although the peripheral image 80 is displayed on the parallax image 61La after enlarging processing so as to overlap the parallax image 61La in FIG. 9, the parallax image 61La after enlarging processing may be displayed on the peripheral image 80 so as to overlap the peripheral image 80. Furthermore, the display screen 60A shown in FIG. 7 and the display screen 60A shown in FIG. 9 may be switched according to an operation of the display switching icon 65*e*.

Figure 10:
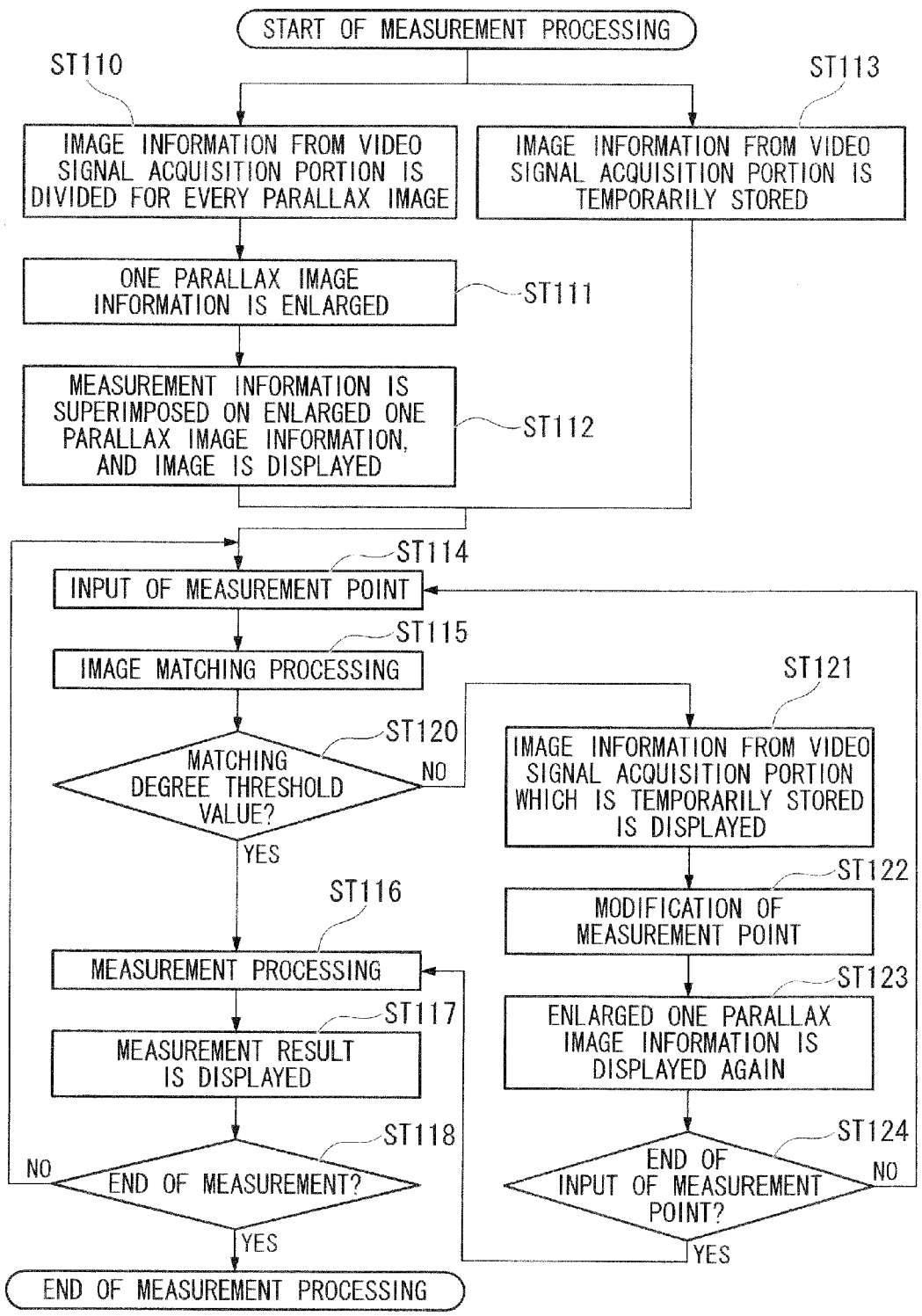
FIG. 10 is a flow chart showing the procedure of an operation (measurement processing) of the endoscope apparatus in a modified example of the first embodiment of the present invention.

In addition, when the matching degree regarding input measuring point is smaller than a predetermined threshold value, the control portion 45 may automatically display both the parallax images 61L and 61R on the display screen of the display portion 33 so as to enable the examiner to modify the measuring point. In this case, as shown in FIG. 10, ST120 to ST124 are added between ST115 and ST116 of FIG. 6.

Figure 11:
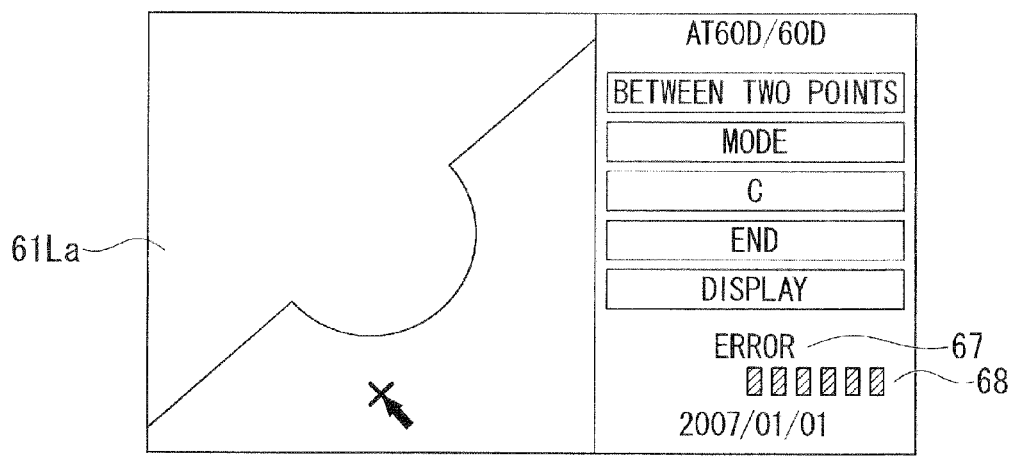
FIG. 11 is a reference view showing a display screen of the endoscope apparatus in the modified example of the first embodiment of the present invention.

In ST120, the control portion 45 compares the matching degree calculated by the image measurement processing portion 43 with a threshold value and checks whether or not the matching degree is equal to or more than the predetermined threshold value. When the matching degree is equal to or more than the predetermined threshold value, the process proceeds to ST116. When the matching degree is smaller than the predetermined threshold value, a message indicating that there was an error in the image matching processing is displayed on the message information 67 as shown in FIG. 11, and proceeds to ST121.

Figure 12:
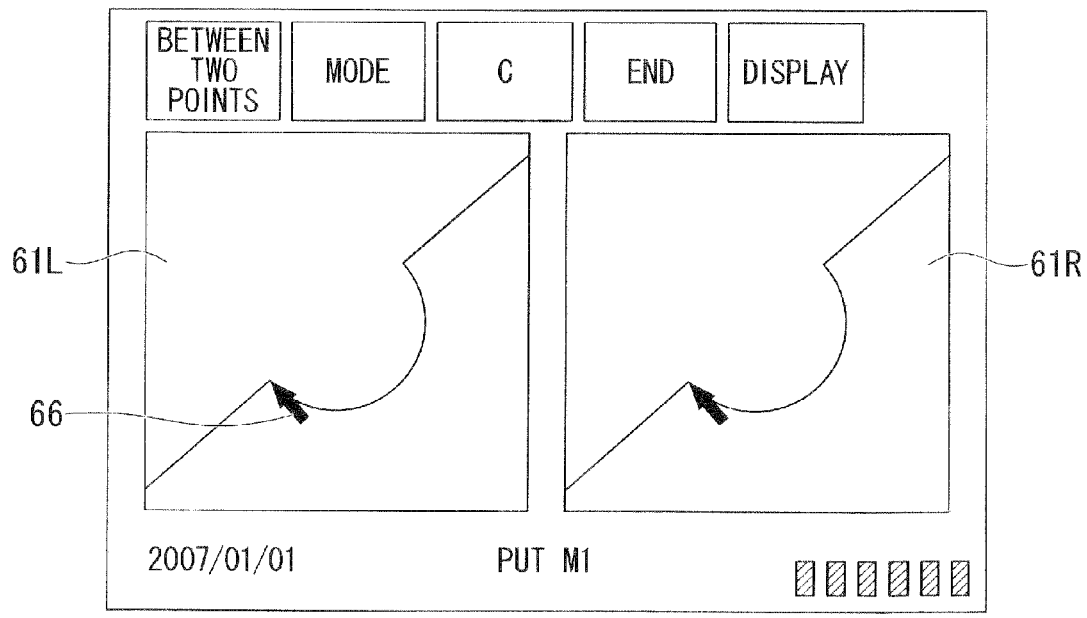
FIG. 12 is a reference view showing a display screen of the endoscope apparatus in the modified example of the first embodiment of the present invention.

In ST121, the control portion 45 executes processing for switching of a display screen. The video signal processing portion 34 outputs a video signal based on the image data including both the parallax images 61L and 61R which are temporarily stored in the image storage portion 42 in ST113, as the output video signal 101A, to the signal conversion portion 38 on the basis of the instruction from the control portion 45. As a result, as shown in FIG. 12, both the parallax images 61L and 61R are displayed on the display screen of the display portion 33.

In ST122, the examiner modifies the measuring point by moving the measurement cursor 66 and selecting a position on the screen with the operation portion 31 while observing the display screen on which both the parallax images 61L and 61R are displayed. Corresponding to the modified position, coordinate information on the parallax images 61L and 61R are acquired again.

Figure 13:
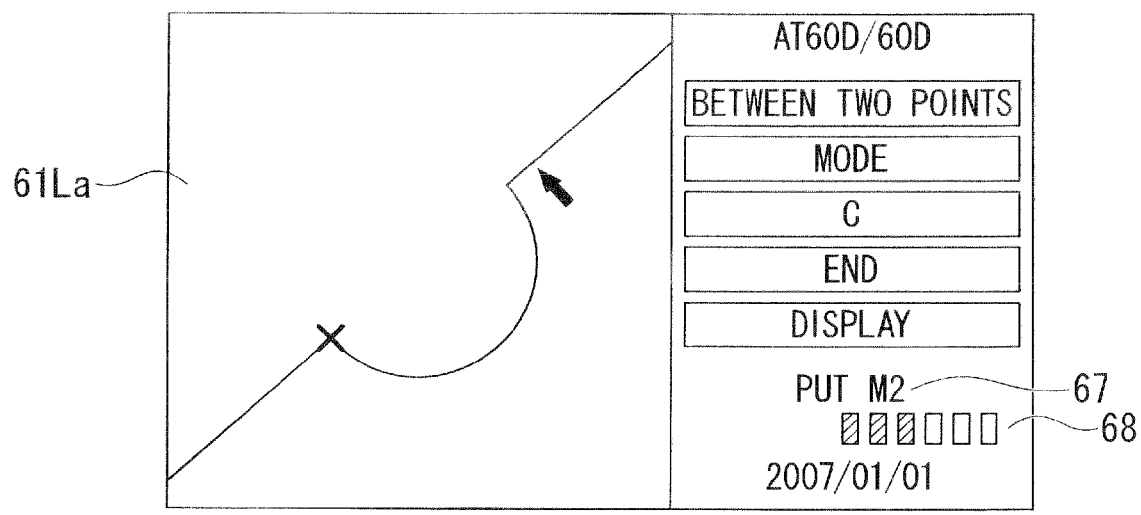
FIG. 13 is a reference view showing a display screen of the endoscope apparatus in the modified example of the first embodiment of the present invention.

In ST123, the control portion 45 executes processing for switching of a display screen. The video signal processing portion 34 outputs a video signal based on the parallax image 61La after enlarging processing, as the output video signal 101A, to the signal conversion portion 38 on the basis of the instruction from the control portion 45. The signal conversion portion 38 superimposes the measurement information 102 after modification on the output video signal 101A and outputs it to the display portion 33 as the display video signal 101a. As a result, as shown in FIG. 13, the parallax image 61La after enlarging processing is displayed again on the display portion 33.

Thus, the measuring point is modified such that the matching degree regarding the measuring point becomes equal to or more than the predetermined threshold value, and the process proceeds to ST124.

In ST124, the control portion 45 checks whether or not an operation for terminating the input of a measuring point in the operation portion 31 has been performed. When the operation for terminating the input of measurement has not been performed, the process proceeds to ST114. In addition, when the operation for terminating the input of a measuring point has been performed, the process proceeds to ST116 in which measurement processing is performed.

That is, ST120 to ST123 are repeated according to the number of measuring points required for measurement.

In addition, when it is determined that the matching degree is smaller than the predetermined threshold value in ST120, the measuring point input in ST114 may be cleared and a measuring point may be input again in ST122.

According to the present embodiment, when the measurement start signal 103 is input from the operation portion 31 during a period (period including at least a part until a point of time at which a measurement result is generated by performing measurement from a point of time at which measurement processing starts) regarding measurement, the parallax image 61La which is subjected to enlarging processing is displayed. The examiner performs an operation, such as input of a measuring point, while observing the display screen on which the parallax image 61La after enlarging processing is displayed. Accordingly, since the visibility of a display image can be improved, it can be expected that the examiner would not be confused about performing an operation, such as input of a measuring point, on which parallax image.

Moreover, the visibility can be further improved by enlarging one parallax image and displaying it.

Figure 14:
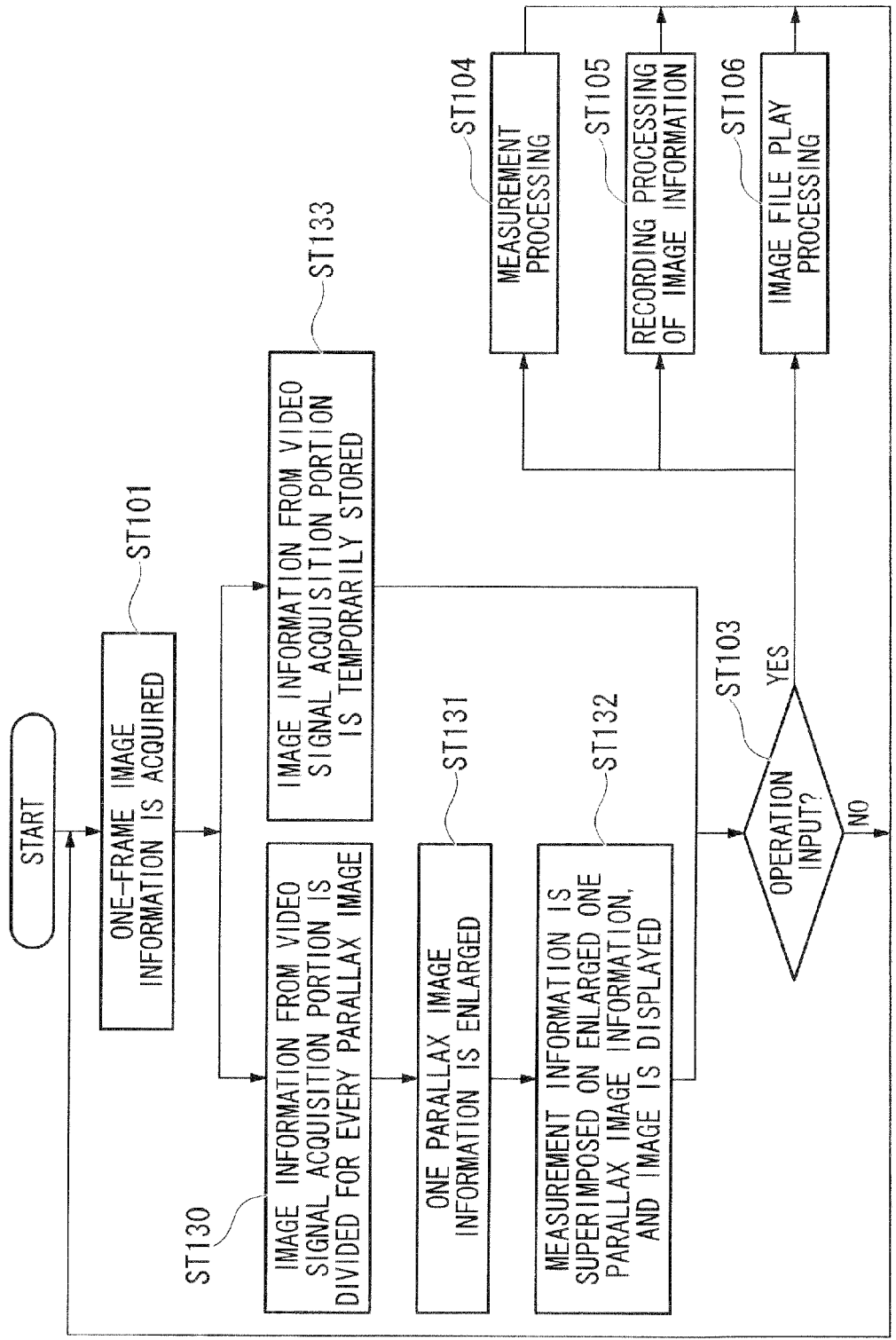
FIG. 14 is a flow chart showing the procedure of an operation (entire processing) of the endoscope apparatus in the modified example of the first embodiment of the present invention.
Figure 15:
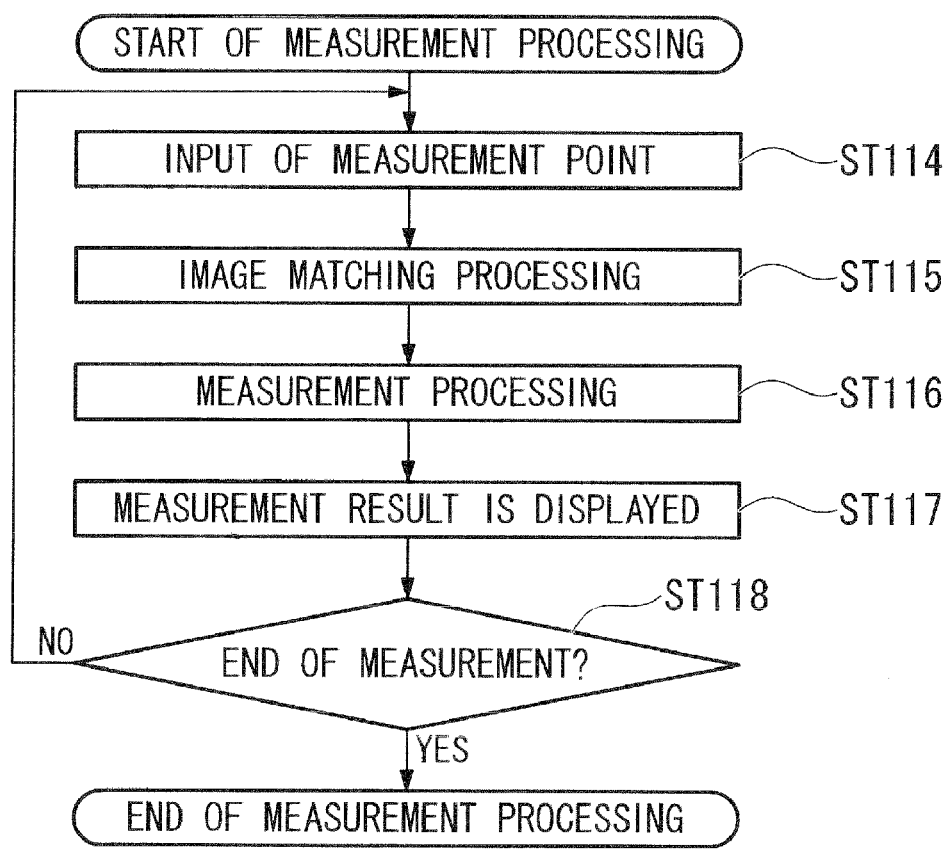
FIG. 15 is a flow chart showing the procedure of an operation (measurement processing) of the endoscope apparatus in the modified example of the first embodiment of the present invention.

FIGS. 14 and 15 show an example where the timing at which one of the two parallax images 61L and 61R are enlarged and displayed is changed.

In ST102 of FIG. 4, a video signal of the one-frame input video signal 100 acquired in S101 is output as the output video signal 101A to the signal conversion portion 38 without any change. That is, when the operation input does not occur, image data including both the parallax images 61L and 61R is displayed on the display portion 33.

However, as shown in FIG. 14, in this modified example, processing of ST130 to ST133 is performed instead of processing of ST102 of FIG. 4 when image information corresponding to one frame is acquired in ST101. In these ST130 to ST133, the same processing as ST110 to ST113 of FIG. 6 is performed. That is, in this modified example, an image of the one-frame input video signal 100 acquired in S101 is divided into the two parallax images 61L and 61R (ST130), enlarging processing is performed on one parallax image 61L (ST131), and one parallax image 61La after enlarging processing is displayed on the display portion 33 (ST132).

Thus, the video signal processing portion 34 may output the parallax image 61La as the output video signal 101A in the image display mode (when a video signal of a subject is displayed in a real-time manner).

At this time, the parallax image 61La is continuously displayed as the output video signal 101A in the measurement mode even if the process proceeds from the image display mode to the measurement mode. That is, in ST103 of FIG. 14, when an operation input for starting the measurement is performed, the process proceeds to ST104. In the measurement processing in this modified example, processing of ST114 to 5118 is performed as shown in FIG. 15. In the image display mode, since processing for displaying one parallax image 61La after enlarging processing has already been performed, the processing equivalent to ST110 to ST113 of FIG. 6 is omitted.

Second Embodiment

Hereinafter, a second embodiment of the present invention will be described with reference to the drawings. Enlarging processing of a parallax image in the second embodiment is different from that in the first embodiment. Although enlarging processing of the entire parallax image 61L is performed automatically in the first embodiment, enlarging processing of a region of the parallax image 61L designated by the examiner is performed in the second embodiment.

Figure 16:
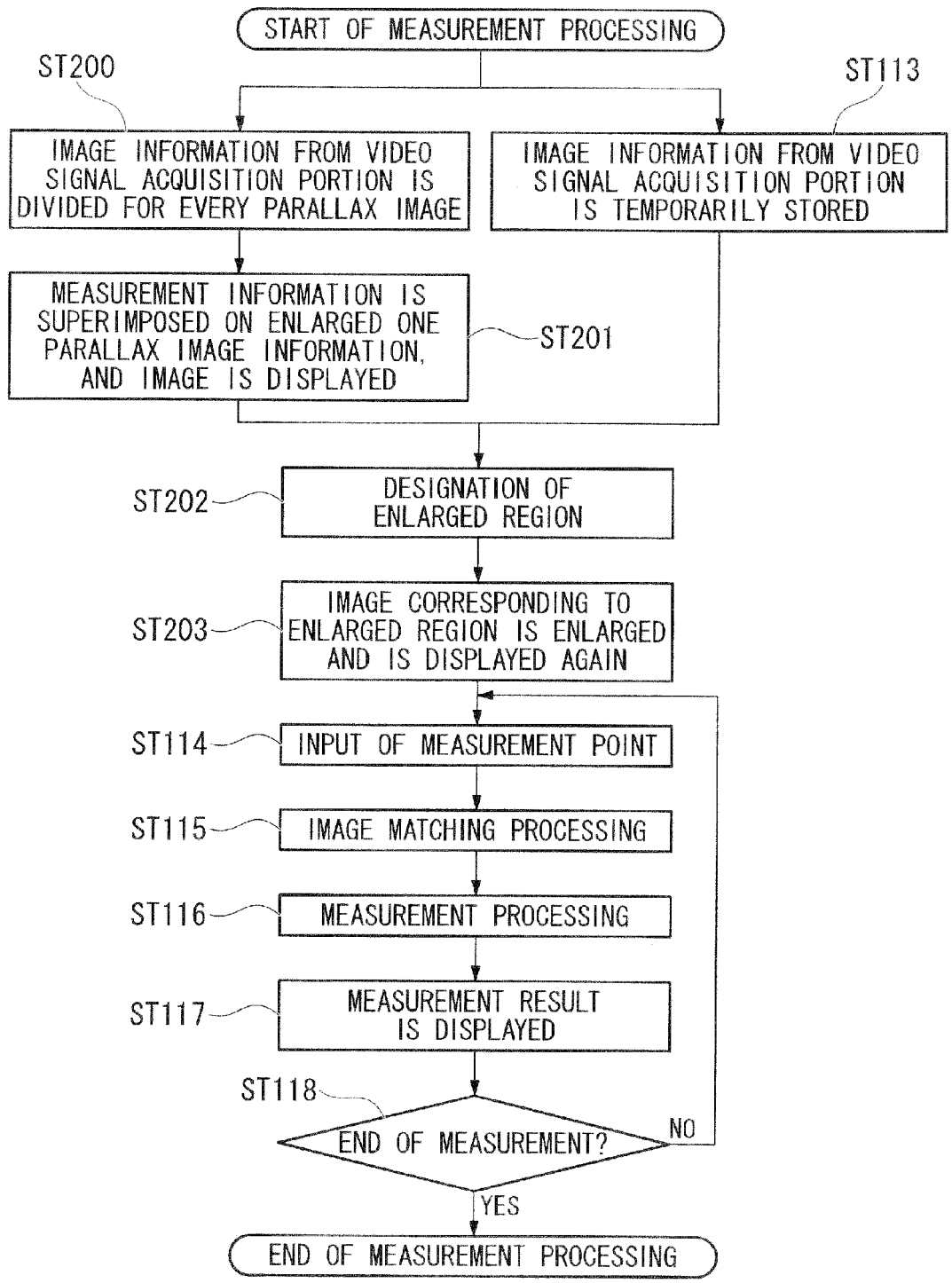
FIG. 16 is a flow chart showing the procedure of an operation (measurement processing) of an endoscope apparatus according to a second embodiment of the present invention.

As shown in FIG. 16, in ST200, the video signal processing portion 34 divides acquired image information for every parallax image by performing processing for dividing an image of the input video signal 100 from the video signal acquisition portion 30 into two parallax images 61L and 61R of FIG. 5. Of the two divided parallax images, a video signal based on one parallax image (parallax image 61L) is output as the output video signal 101A to the signal conversion portion 38.

Then, in ST201, the signal conversion portion 38 superimposes the measurement information 102, which is generated in the image measurement processing portion 43, on the output video signal 101A based on the parallax image 61L and outputs it to the display portion 33 as the display video signal 101a. The display portion 33 displays the parallax image 61L on the basis of the display video signal 101a.

ST113 is processed in parallel with the above-described ST200 and ST201. Processing of ST113 is the same as that in the first embodiment.

Figure 17:
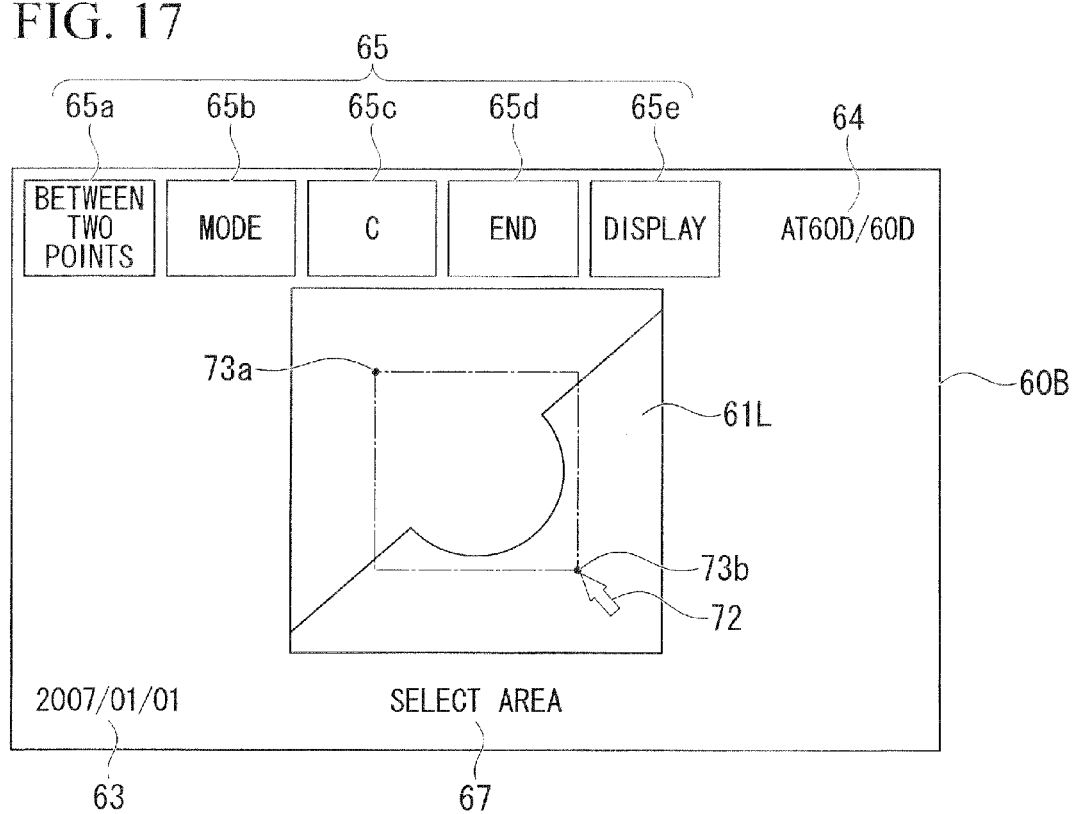
FIG. 17 is a reference view showing a display screen of the endoscope apparatus according to the second embodiment of the present invention.

FIG. 17 shows a display screen 60B at the start of such measurement mode. The parallax image 61L, the date information 63, the measurement condition information 64, the operation icon 65, the message information 67, an enlargement cursor 72, and the like are displayed on the display screen 60B.

The display screen 60B is configured to include a display region, which is disposed approximately in the middle of the display screen 60B and has the same size as the display region where the parallax image 61L is displayed on the display screen 60 shown in FIG. 5, and a frame-shaped display region surrounding the display region.

The parallax image 61L is displayed in the approximately middle display region of the display screen 60B. In addition, the date information 63, the measurement condition information 64, the operation icon 65, the message information 67, and the like are displayed in upper and lower portions of the frame-shaped display region.

The enlargement cursor 72 serves to designate an enlarged region on the display screen 60B in response to an operation input from the operation portion 31. The enlargement cursor 72 is displayed so as to overlap the parallax image 61L.

As shown in FIG. 16, after the above-described ST200 and ST201 end, the process proceeds to ST202. In ST202, a region to be enlarged on the parallax image 61L is designated. First, as shown in FIG. 17, a message that requests designation of an enlarged region is displayed as the message information 67, and the control portion 45 receives the input of an enlarged region. The examiner inputs an enlarged region by moving the enlargement cursor 72 and selecting two arbitrary points 73a and 73b on the screen with the operation portion 31 while observing the display screen 60B of the display portion 33 on which the parallax image 61L is displayed. A rectangle having a line segment, which connects the selected two points 73a and 73b, as a diagonal line is designated as the enlarged region. Information on the designated enlarged region is output to the video signal processing portion 34.

Figure 18:
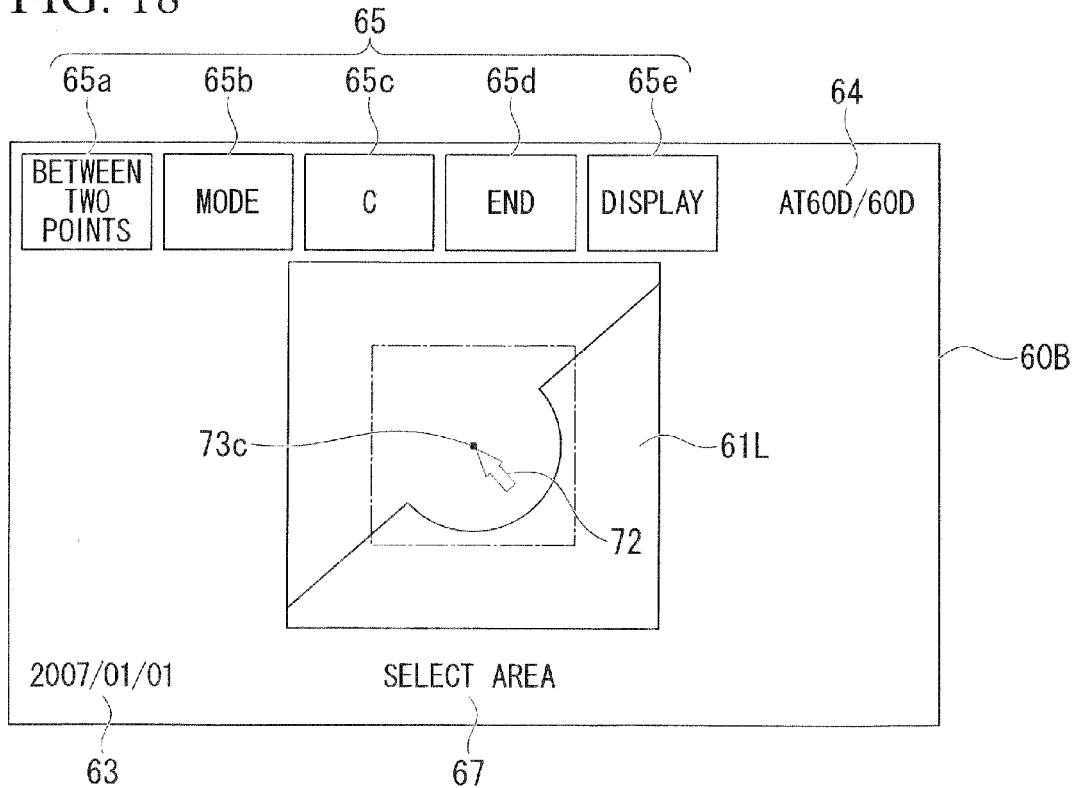
FIG. 18 is a reference view showing a display screen of the endoscope apparatus according to the second embodiment of the present invention.

As shown in FIG. 18, in ST202, the examiner may input an enlarged region by moving the enlargement cursor 72 and selecting one arbitrary point 73c on the screen with the operation portion 31 while observing the display screen 60B of the display portion 33 on which the parallax image 61L is displayed. In this case, a predetermined region having the selected one point 73c as the center is designated as the enlarged region.

In ST203, the video signal processing portion 34 performs enlarging processing on the parallax image 61L on the basis of the information on the enlarged region in ST202. A video signal based on the parallax image 61La after enlarging processing is output as the output video signal 101A to the signal conversion portion 38. The signal conversion portion 38 superimposes the measurement information 102, which is generated in the image measurement processing portion 43, on the output video signal 101A based on the parallax image 61La after enlarging processing, and outputs it to the display portion 33 as the display video signal 101a. The display portion 33 displays the parallax image 61La after enlarging processing, instead of the parallax image 61L, on the basis of the display video signal 101a.

Figure 19:
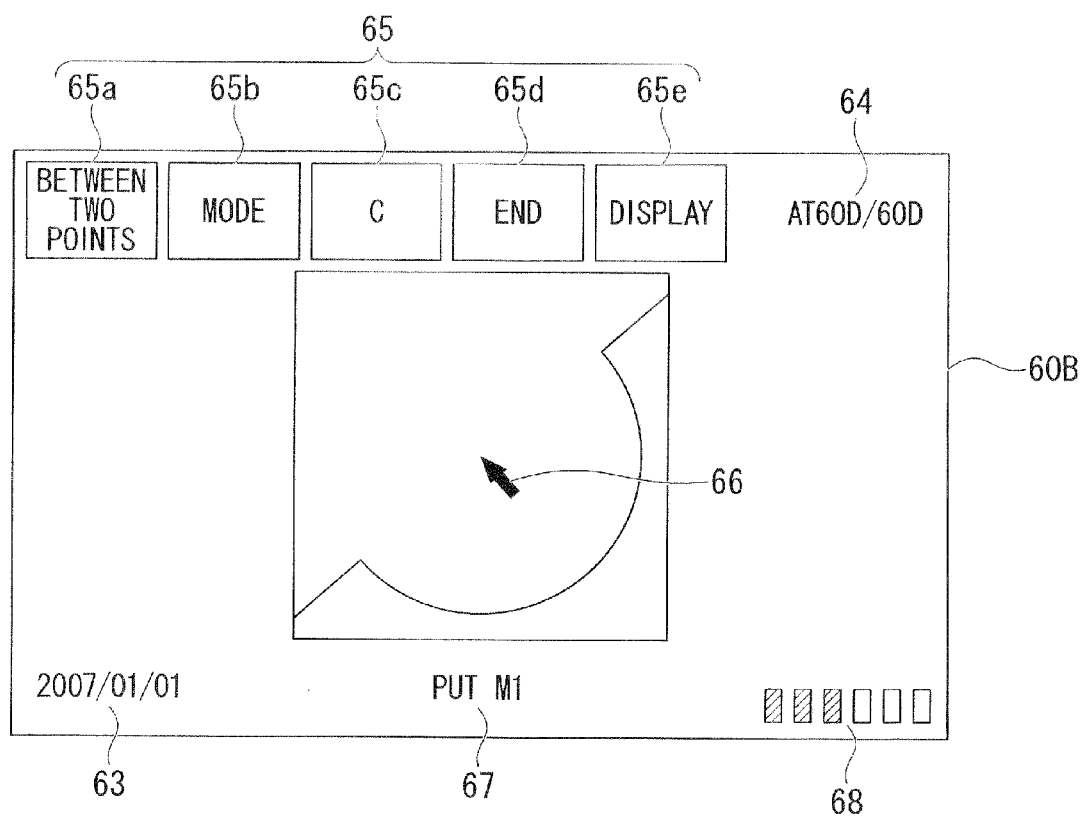
FIG. 19 is a reference view showing a display screen of the endoscope apparatus according to the second embodiment of the present invention.

FIG. 19 shows a display screen 60C after enlarging processing in such ST202 and ST203. The parallax image 61La after enlarging processing, the date information 63, the measurement condition information 64, the operation icon 65, the measurement cursor 66, the message information 67, the image matching degree information 68, and the like are displayed on the display screen 60C.

Similar to the display screen 60B of FIG. 17, the display screen 60C is configured to include a display region, which is disposed approximately in the middle of the display screen 60C and has the same size as the display region where the parallax image 61L is displayed on the display screen 60 shown in FIG. 5, and a frame-shaped display region surrounding the display region.

The parallax image 61La after enlarging processing is displayed in the approximately middle display region of the display screen 60C. In addition, the date information 63, the measurement condition information 64, the operation icon 65, the message information 67, the image matching degree information 68, and the like are displayed in upper and lower portions of the frame-shaped display region. The measurement cursor 66 is displayed so as to overlap the parallax image 61La after enlarging processing.

Figure 20:
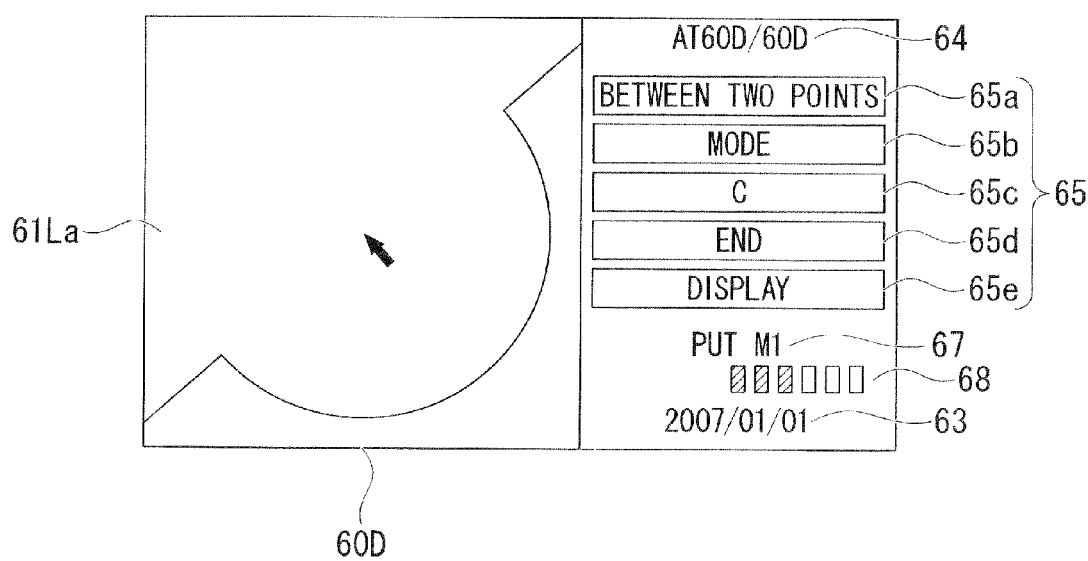
FIG. 20 is a reference view showing a display screen of the endoscope apparatus according to the second embodiment of the present invention.

As shown in FIG. 20, the signal conversion portion 38 may change the display form (display position of a menu and the like) before and after enlargement, such that a display screen 60D after enlarging processing is configured to include two approximately rectangular display regions disposed on the left and right sides similar to the display screen 60A shown in FIG. 7. In this case, the parallax image 61La after enlarging processing is displayed in the left display region of the display screen 60D. The date information 63, the measurement condition information 64, the operation icon 65, the message information 67, the image matching degree information 68, and the like are displayed in the right display region of the display screen 60D. The measurement cursor 66 is displayed so as to overlap the parallax image 61La after enlarging processing.

After the above-described ST203 ends, the process proceeds to ST114. Processing of ST114 to ST118 is the same as that in the first embodiment.

According to the present embodiment, when the examiner designates an enlarged region during a period (period including at least a part until a point of time at which a measurement result is generated by performing measurement from a point of time at which measurement processing starts) regarding measurement, a region of the parallax image 61L designated by the examiner is subjected to enlarging processing and is displayed as the parallax image 61La. The examiner performs an operation, such as input of a measuring point, while observing the display screen on which the parallax image 61La after enlarging processing is displayed. Therefore, also in the present embodiment, the same effect as in the first embodiment can be obtained. In addition, according to present embodiment, since the examiner can arbitrarily designate an enlarged region of the parallax image 61L, the visibility can be further improved.

The enlargement cursor 72 may be displayed to have a shape, a color, and the like different from the measurement cursor 66. Moreover, the image matching degree information 68 may not be displayed at the time of designation of an enlarged region.

Modified Example of the Second Embodiment

Hereinafter, a modified example of the second embodiment of the present invention will be described with reference to the drawings.

Figure 21:
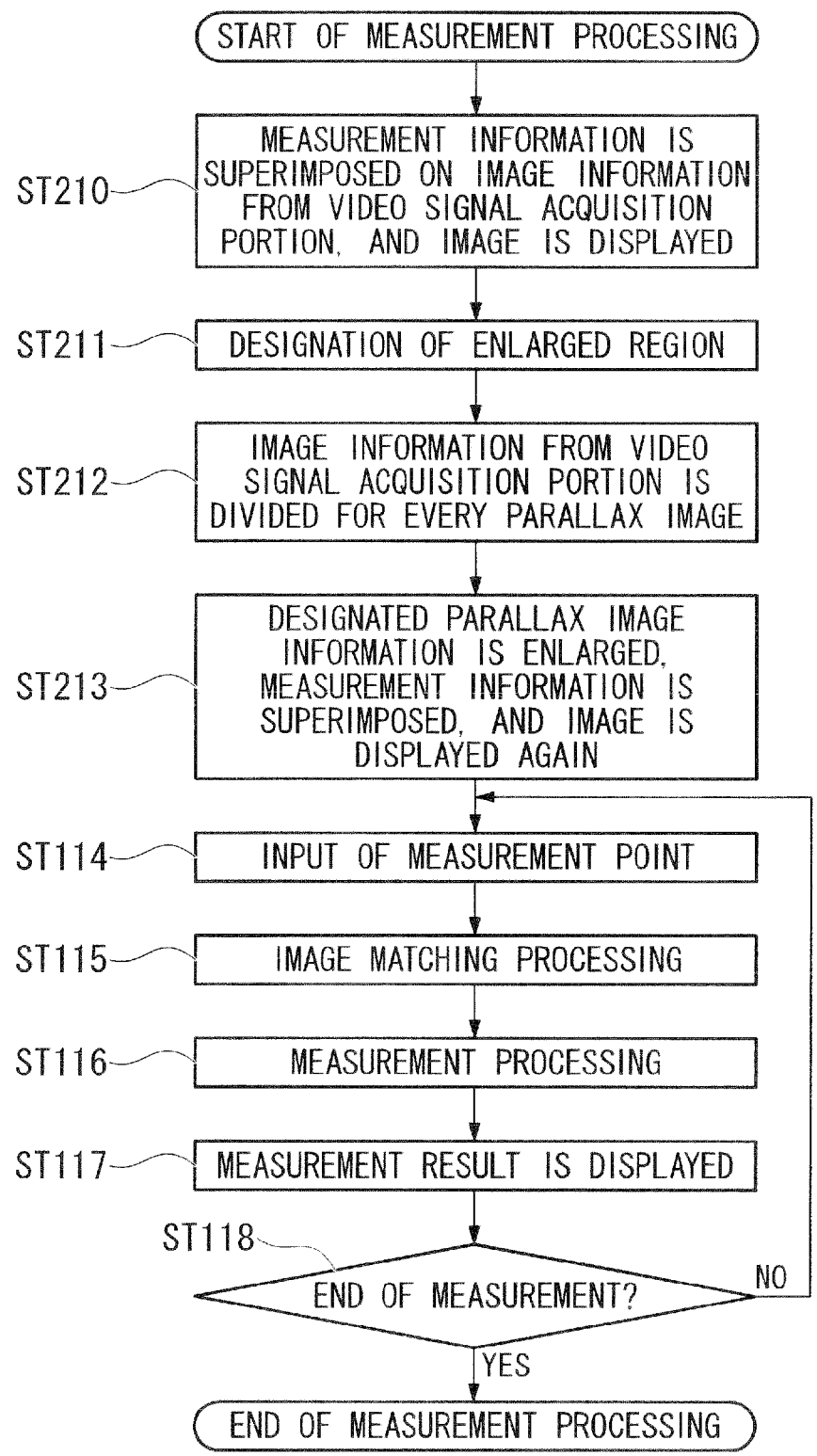
FIG. 21 is a flow chart showing the procedure of an operation (measurement processing) of an endoscope apparatus in a modified example of the second embodiment of the present invention.

As shown in FIG. 21, in ST210, the video signal processing portion 34 outputs the input video signal 100 from the video signal acquisition portion 30, as the output video signal 101A, to the signal conversion portion 38 without any change. That is, in this modified example, a video signal based on the parallax images 61L and 61R is output as the output video signal 101A to the signal conversion portion 38. Then, the signal conversion portion 38 superimposes the measurement information 102, which is generated in the image measurement processing portion 43, on the output video signal 101A based on the parallax images 61L and 61R and outputs it to the display portion 33 as the display video signal 101a. The display portion 33 displays the parallax images 61L and 61R on the basis of the display video signal 101a.

Figure 22:
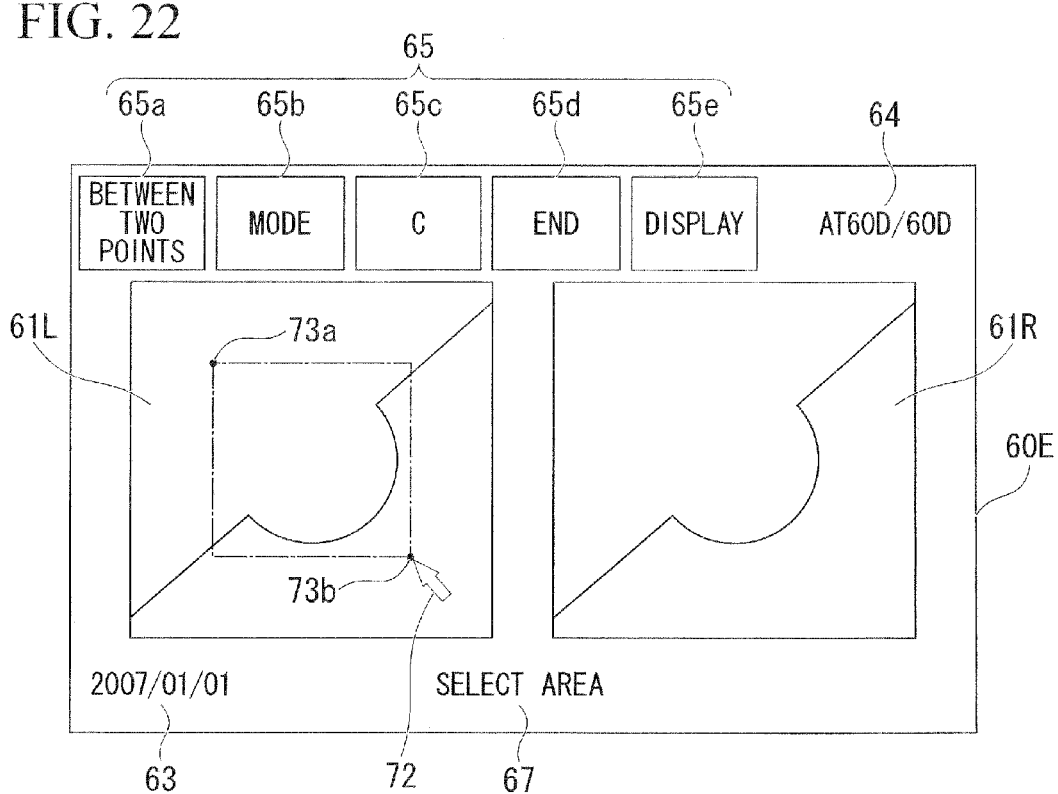
FIG. 22 is a reference view showing a display screen of the endoscope apparatus in the modified example of the second embodiment of the present invention.

FIG. 22 shows a display screen 60E at the start of such measurement mode. The parallax images 61L and 61R, the date information 63, the measurement condition information 64, the operation icon 65, the message information 67, the enlargement cursor 72, and the like are displayed on the display screen 60E. The parallax images 61L and 61R, the date information 63, the measurement condition information 64, the operation icon 65, the message information 67, and the like are displayed in the same manner as the display image 60 of FIG. 5. The enlargement cursor 72 is displayed so as to overlap the parallax image 61L.

In ST211, a region to be enlarged is designated on the parallax image 61L. First, as shown in FIG. 22, a message that requests designation of an enlarged region is displayed as the message information 67, and the control portion 45 receives the input of an enlarged region. The examiner inputs an enlarged region by moving the enlargement cursor 72 and selecting two arbitrary points 73a and 73b on the screen with the operation portion 31 while observing the display screen 60E of the display portion 33 on which the parallax image 61L is displayed. A rectangle having a line segment, which connects the selected two points 73a and 73b, as a diagonal line is designated as the enlarged region. Information on the designated enlarged region is output to the video signal processing portion 34.

Then, in ST212, the video signal processing portion 34 divides acquired image information for every parallax image by performing processing for dividing an image of the input video signal 100 from the video signal acquisition portion 30 into two parallax images 61L and 61R of FIG. 5.

Then, in ST213, the video signal processing portion 34 performs processing for enlarging one parallax image (parallax image 61L) of the two parallax images divided in ST212 on the basis of the information on the enlarged region in ST211. A video signal based on the parallax image 61La after enlarging processing is output as the output video signal 101A to the signal conversion portion 38. The signal conversion portion 38 superimposes the measurement information 102, which is generated in the image measurement processing portion 43, on the output video signal 101A based on the parallax image 61La after enlarging processing and outputs it to the display portion 33 as the display video signal 101a. The display portion 33 displays the parallax image 61La after enlarging processing, instead of the parallax images 61L and 61R, on the basis of the display video signal 101a.

Figure 23:
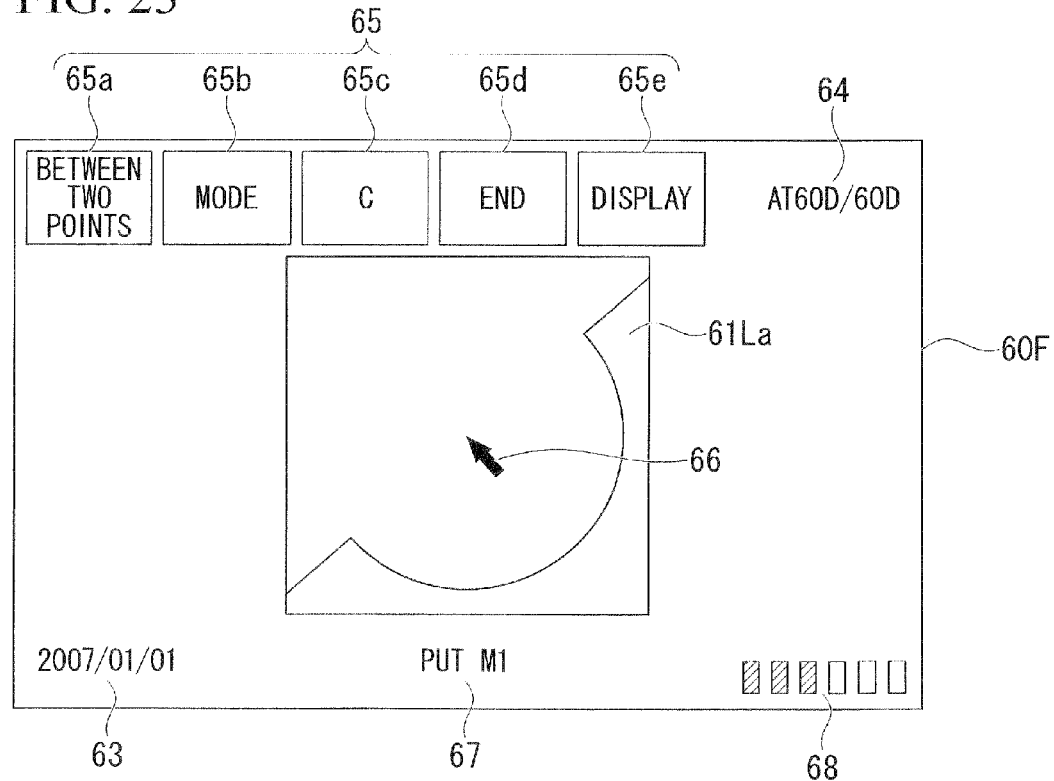
FIG. 23 is a reference view showing a display screen of the endoscope apparatus in the modified example of the second embodiment of the present invention.

FIG. 23 shows a display screen 60F after enlarging processing in such ST211 to ST213. The parallax image 61La after enlarging processing, the date information 63, the measurement condition information 64, the operation icon 65, the measurement cursor 66, the message information 67, and the like are displayed on the display screen 60F.

For example, similar to the display screen 60B of FIG. 17, the display screen 60F is configured to include a display region, which is disposed approximately in the middle of the display screen 60F and has the same size as the display region where the parallax image 61L is displayed on the display screen 60 shown in FIG. 5, and a frame-shaped display region surrounding the display region.

The parallax image 61La after enlarging processing is displayed in the approximately middle display region of the display screen 60F. In addition, the date information 63, the measurement condition information 64, the operation icon 65, the message information 67, and the like are displayed in upper and lower portions of the frame-shaped display region. The measurement cursor 66 is displayed so as to overlap the parallax image 61La after enlarging processing.

After the above-described ST213 ends, the process proceeds to ST114. Processing of ST114 to ST118 is the same as that in the second embodiment.

As described above, also in the modified example of the second embodiment, the same effect as in the second embodiment can be obtained.

Figure 24:
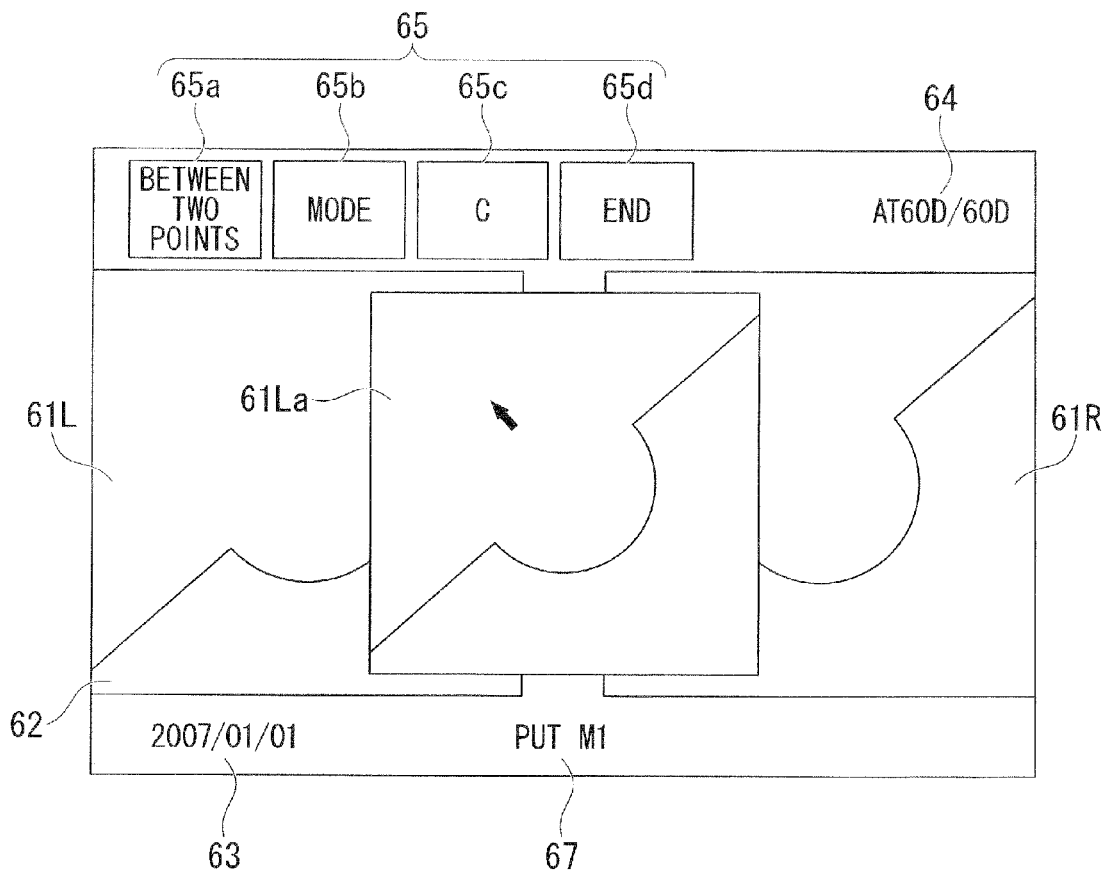
FIG. 24 is a reference view showing a display screen of the endoscope apparatus in the modified example of the second embodiment of the present invention.

Moreover, in ST213, as shown in FIG. 24, a video signal based on the parallax image 61La may be output as the output video signal 101A to the signal conversion portion 38 together with the input video signal 100. The signal conversion portion 38 superimposes the measurement information 102, which is generated in the image measurement processing portion 43, on the output video signal 101A from the video signal processing portion 34 and outputs it to the display portion 33 as the display video signal 101a. In this case, the display portion 33 displays the enlarged parallax image 61La together with the parallax images 61L and 61R on the basis of the display video signal 101a.

In this case, since the parallax images 61L and 61R and the parallax image 61La which is superimposed on the parallax images 61L and 61R are displayed on the same display screen, it can be expected that the examiner will pay attention to the enlarged parallax image 61La while seeing the entire of the parallax images.

Third Embodiment

Hereinafter, a third embodiment of the present invention will be described with reference to the drawings. The present embodiment relates to storage processing of image information and play processing of an image file, that is, an operation when an operation input for recording image information or an operation input for playing an image file is performed as the operation input in ST102 of FIG. 4.

Figure 25:
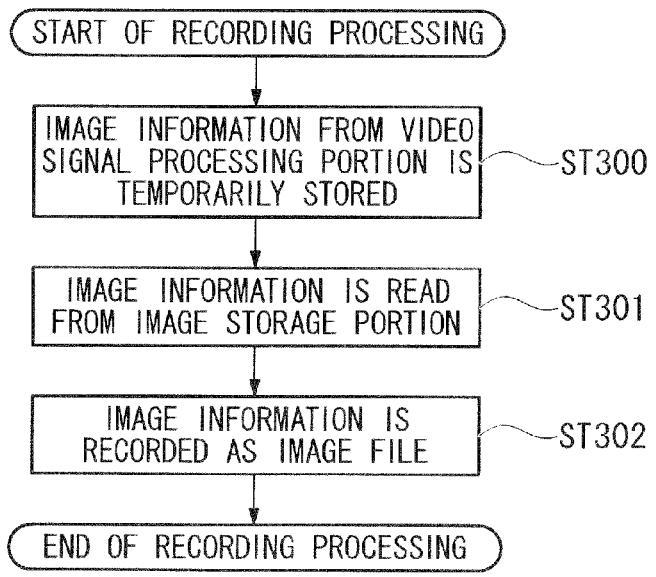
FIG. 25 is a flow chart showing the procedure of an operation (recording processing) of an endoscope apparatus according to a third embodiment of the present invention.

First, an operation when an operation input for recording image information is performed as the operation input in ST102 of FIG. 4 will be described. When the image recording signal 104 is input from the operation portion 31, recording processing shown in FIG. 25 is performed as ST105. Even during the execution of ST104 in FIG. 4, it is possible to receive the recording processing of ST105 by the operation input and to execute it.

In ST300, the video signal processing portion 34 outputs the input video signal 100 from the video signal acquisition portion 30, as the output video signal 101B, to the image storage portion 42 without any change. That is, a video signal corresponding to the parallax images 61L and 61R is temporarily stored in the image storage portion 42.

In ST301, the video signal that is temporarily stored in the image storage portion 42 in ST300 is read from the image storage portion 42 according to the control of the control portion 45. In ST302, the video signal read from the image storage portion 42 in ST301 is recorded as an image file in the storage medium 44, such as the PCMCIA memory card 18 or the compact flash (registered trademark) memory card 19 connected to the PC card interface 13. At this time, the video signal may be recorded distinctively as a separate image file.

Figure 26:
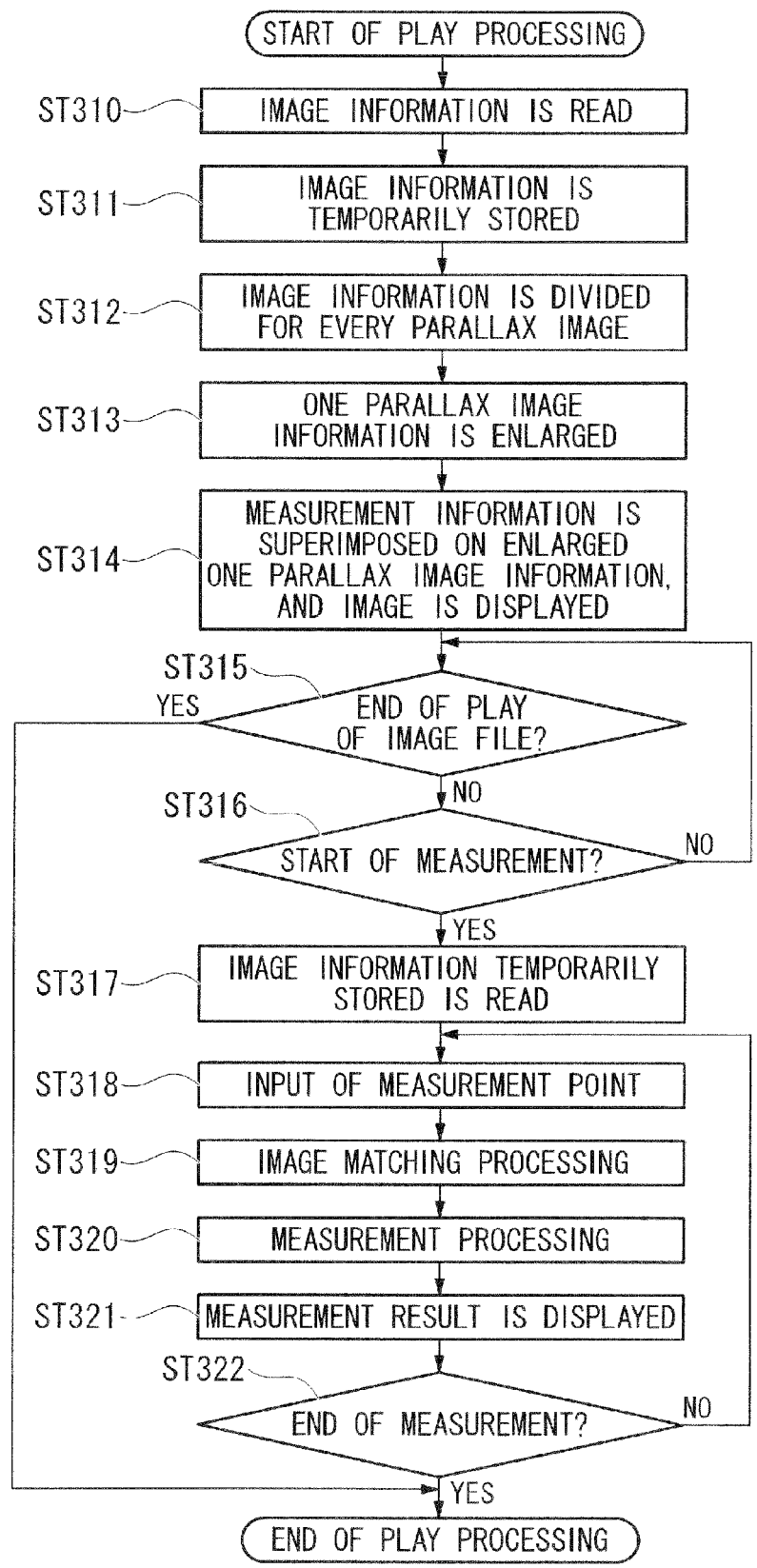
FIG. 26 is a flow chart showing the procedure of an operation (play processing) of the endoscope apparatus according to the third embodiment of the present invention.

Next, an operation when an operation input for playing an image file is performed as the operation input in ST102 of FIG. 4 will be described. When an operation input for playing the image file is performed, play processing shown in FIG. 26 is performed as ST106. In FIG. 4, the play processing of ST106 cannot be executed in parallel with the measurement processing of ST104 or the recording processing of ST105. When an operation input for play processing is performed during processing of the measurement processing or the recording processing, the control portion 45 stops these processings and executes the play processing.

In ST310, for example, a selection menu, such as an image file list, is displayed on the display screen 60. The examiner selects an image file (image information) to be played using the remote controller 5 and the like. The selected video signal is read from the storage medium 44 according to the control of the control portion 45. This video signal is the same as the output video signal 101B stored in the storage medium 44 in step ST302 of FIG. 21. In ST311, the video signal read from the storage medium 44 is temporarily stored in the image storage portion 42.

In ST312, the video signal temporarily stored in the image storage portion 42 is output to the video signal processing portion 34. The video signal processing portion 34 divides acquired image information for every parallax image by performing processing for dividing an image of the video signal from the image storage portion 42 into two parallax images 61L and 61R.

In ST313, similar to ST111, the video signal processing portion 34 performs processing for enlarging one parallax image (parallax image 61L) of the two parallax images divided in ST312. A video signal based on the parallax image 61La after enlarging processing is output as the output video signal 101A to the signal conversion portion 38.

In ST314, the signal conversion portion 38 superimposes the measurement information 102, which is generated in the image measurement processing portion 43, on the output video signal 101A based on the parallax image 61La after enlarging processing and outputs it to the display portion 33 as the display video signal 101*a*. A display screen at this time is the same as the display screen 60A of FIG. 7 except that the display screen is not real-time display but still image display unlike the image display mode. In this case, for example, modifications for displaying the date at the time of recording as the date information 63 or displaying text information for identifying an image file or an icon indicating the image play mode on the display screen 60 so as to overlap the display screen 60 may be suitably performed.

In ST315, the control portion 45 checks whether or not an operation input for terminating play of an image file has been performed in the operation portion 31. When the operation input for terminating play of the image file has been performed, the play processing ends and the process proceeds to ST101 of FIG. 4. Thus, for example, when it is only an object to see an image of an object, which was recorded in the past, on the display portion 33, the examiner can perform an operation input for terminating play of the image file after observing the image of the object and then return to the image display mode. When an operation input for terminating play of an image file in ST315 has not been performed, the process proceeds to ST316.

In ST316, the control portion 45 checks whether or not an operation input for starting measurement has been performed in the operation portion 31. When the operation input for starting the measurement is performed, the process proceeds to ST317. When the operation input for starting the measurement has not been performed, the process proceeds to ST315.

ST317 to ST322 show measurement processing in which image measurement is performed using the video signal stored in the image storage portion 42. Hereinafter, an explanation will be made focusing on a different point from the measurement processing of ST110 to ST118 of FIG. 6.

In ST317, the video signal temporarily stored in the image storage portion 42 in ST311 is read and is output to the video signal processing portion 34 according to the control of the control portion 45.

In ST318, the same processing as ST114 of FIG. 6 is performed. In ST319 to ST321, the same processing as ST115 to ST117 of FIG. 6 is performed. That is, in ST320, the image measurement processing portion 43 performs measurement processing using still image data based on the video signal read in ST310. Moreover, in ST321, the signal conversion portion 38 superimposes the measurement information 102, which is generated in the image measurement processing portion 43, on the output video signal 101A based on the parallax image 61L from the video signal processing portion 34 and outputs it to the display portion 33 as the display video signal 101*a*. The display portion 33 displays the parallax image 61L on the basis of the display video signal 101*a*. In ST322, the same processing as ST118 of FIG. 6 is performed.

Fourth Embodiment

Hereinafter, a fourth embodiment of the present invention will be described with reference to the drawings. Similar to the third embodiment, the present embodiment relates to storage processing of image information and play processing of an image file, that is, an operation when an operation input for recording image information or an operation input for playing an image file is performed as the operation input in ST102 of FIG. 4. In the present embodiment, a display image and a measurement image are recorded separately from each other.

Figure 27:
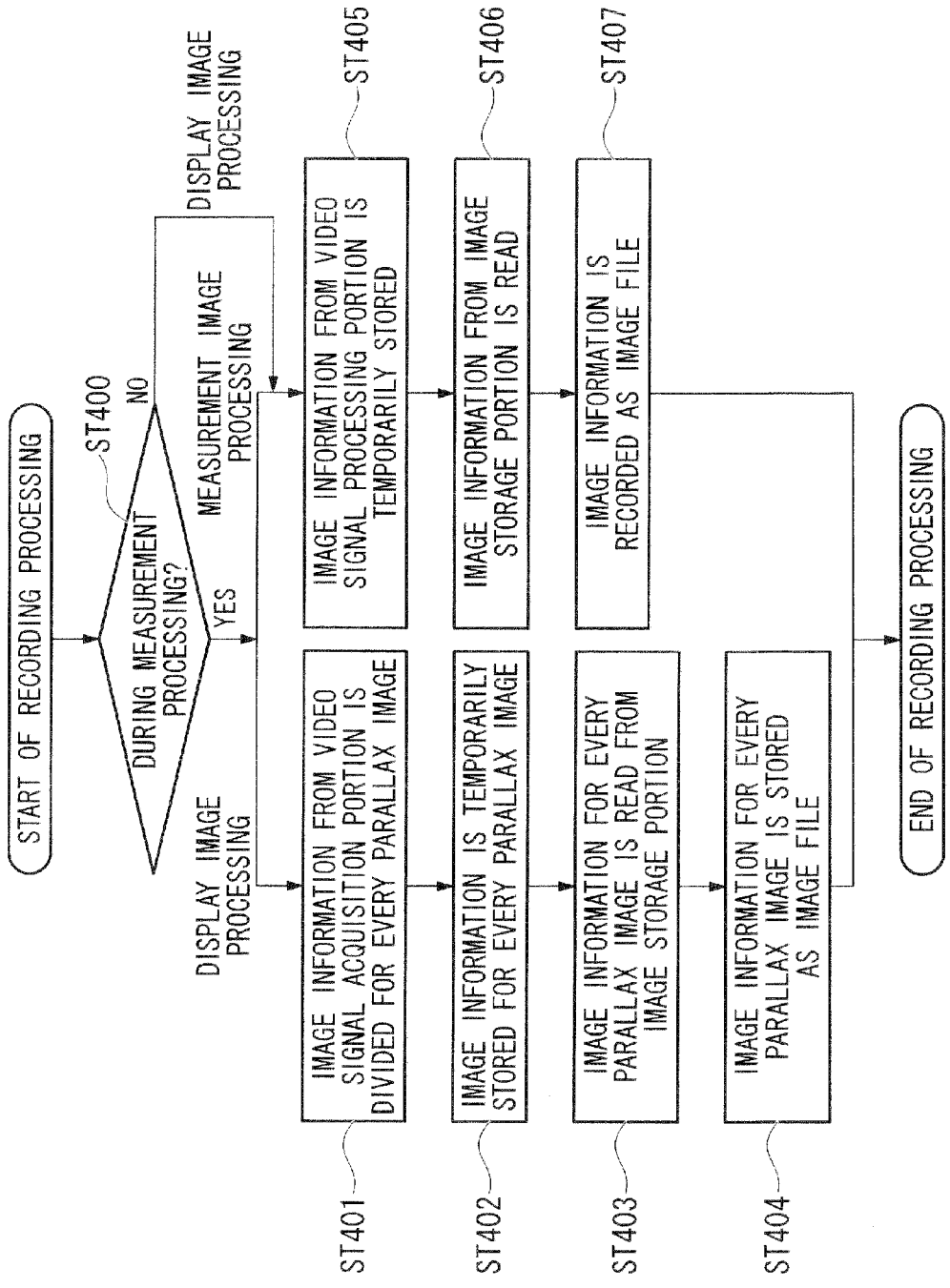
FIG. 27 is a flow chart showing the procedure of an operation (recording processing) of an endoscope apparatus according to a fourth embodiment of the present invention.

First, an operation when an operation input for recording image information is performed as the operation input in ST102 of FIG. 4 will be described. When the image recording signal 104 is input from the operation portion 31, recording processing shown in ST400 to ST407 in FIG. 27 is performed as ST105. Even during the execution of ST104 in FIG. 4, the control portion 45 can receive the recording processing of ST105 by the operation input and execute it.

In ST400, the control portion 45 checks whether or not measurement processing is being performed. If the measurement processing is being performed, the process proceeds to ST401 and ST405. If the measurement processing is not being performed, the process proceeds to ST405.

An operation when it is checked that the measurement processing is being performed in ST400 is as follows.

Processing of ST401 to ST404 is processing regarding recording of a display image and processing of ST405 to ST407 is processing regarding recording of a measurement image or a display image, and the processing of ST401 to ST404 and the processing of ST405 to ST407 are executed simultaneously and in parallel through two systems. In ST401, the video signal processing portion 34 divides acquired image information for every parallax image by performing processing for dividing an image of the input video signal 100 from the video signal acquisition portion 30 into two parallax images 61L and 61R of FIG. 6. A video signal based on one (in this example, the parallax image 61L) of the two divided parallax images is output as the output video signal 101B to the image storage portion 42.

In ST402, a video signal corresponding to the parallax image 61L divided in ST401 is stored in the image storage portion 42. When division of image information has been already performed in ST104 of FIG. 4, the video signal which is obtained as the processing result is used in subsequent processing.

In ST403, the video signal, which is temporarily stored in the image storage portion 42 in ST402, is read from the image storage portion 42 according to the control of the control portion 45. In ST404, the video signal read from the image storage portion 42 in ST403 is recorded as an image file in the storage medium 44, such as the PCMCIA memory card 18 or the compact flash (registered trademark) memory card 19 connected to the PC card interface 13. At this time, the video signal may be recorded distinctively as a separate image file.

On the other hand, in ST405, the output video signal 101B based on image data including both the parallax images 61L and 61R is output from the video signal processing portion 34 to the image storage portion 42, and the image information is temporarily stored in the image storage portion 42. When storage of the video signal has been already performed in the measurement processing ST104, the video signal is used in subsequent processing.

In ST406, the video signal, which is temporarily stored in the image storage portion 42 in ST405, is read according to the control of the control portion 45. Then, in ST407, the video signal read from the image storage portion 42 in ST406 is recorded as an image file in the storage medium 44, such as the PCMCIA memory card 18 or the compact flash (registered trademark) memory card 19 connected to the PC card interface 13. At this time, the video signal may be recorded distinctively as a separate image file.

Moreover, in ST400, when it is checked that the measurement processing is not being performed, processing (ST405 to ST407) regarding recording of a display image is performed.

Figure 28:
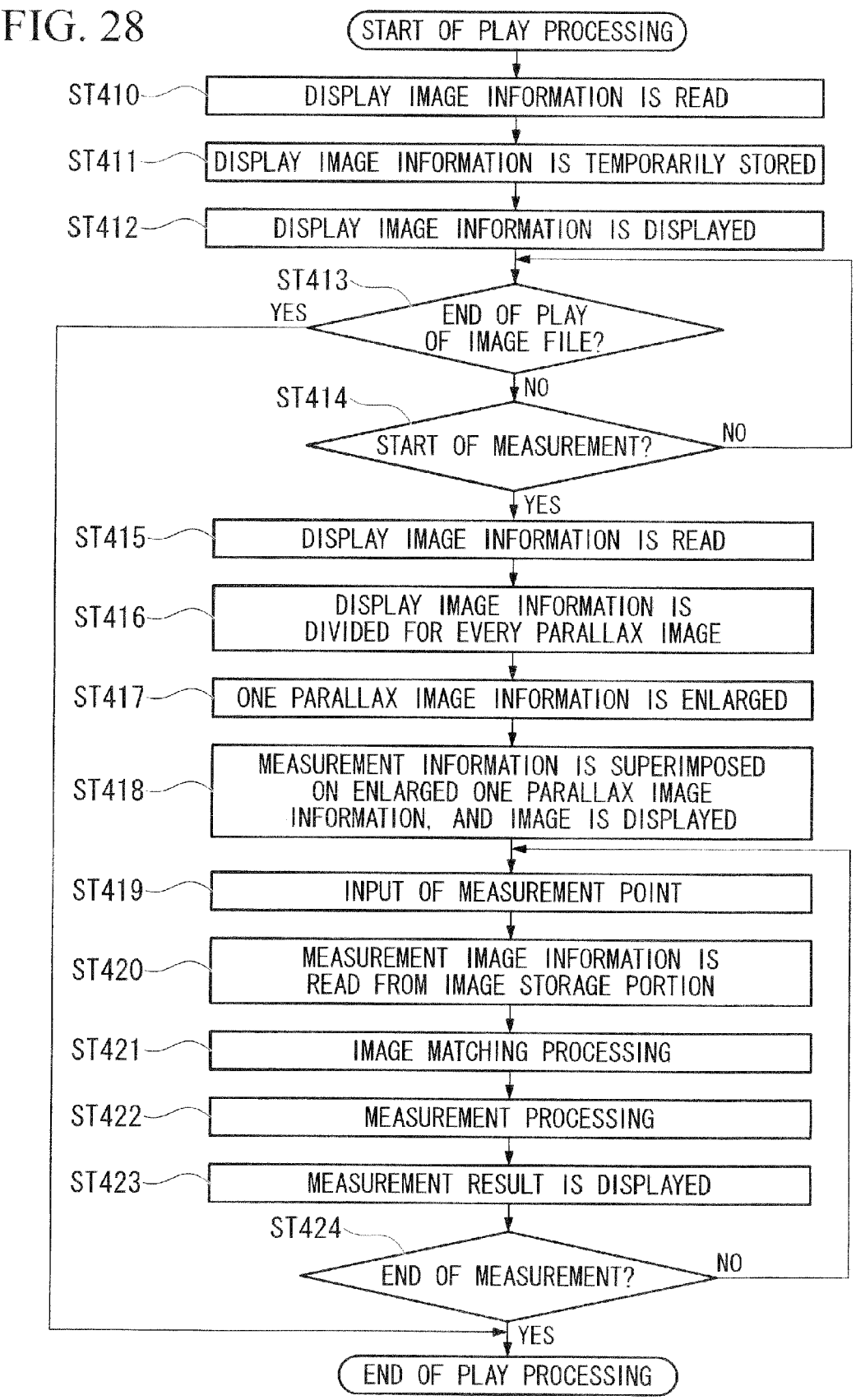
FIG. 28 is a flow chart showing the procedure of an operation (play processing) of the endoscope apparatus according to the fourth embodiment of the present invention.

Next, an operation when an operation input for playing an image file is performed as the operation input in ST102 of FIG. 4 will be described. When an operation input for playing an image file is performed, play processing shown in ST410 to ST424 in FIG. 28 is performed as ST106. In FIG. 4, the play processing of ST106 cannot be executed in parallel with the measurement processing of ST104 or the recording processing of ST105. When an operation input of play processing is performed during processing of the measurement processing or the recording processing, these processings are stopped to execute the play processing.

In ST410, for example, a selection menu, such as an image file list, is displayed on the display screen 60. A video signal that the examiner selected as an image file (display image information), which is to be played, using the remote controller 5 is read from the storage medium 44 according to the control of the control portion 45. This video signal is the same as the output video signal 101A at the time of recording and is stored in the storage medium 44 as a measurement video signal or a display video signal in step ST407 of FIG. 27. In ST411, the video signal read from the storage medium 44 is temporarily stored as the display video signal in the image storage portion 42.

In ST412, the display video signal stored in the image storage portion 42 in ST411 is output from the image storage portion 42 to the signal conversion portion 38, the display video signal 101a is output from the signal conversion portion 38 to the display portion 33, and an image is displayed on the display portion 33. A display screen at this time is the same as the display screen 60 of FIG. 5 except that the display screen is not real-time display in the image display mode but still image display. Moreover, the video signal stored in the storage medium 44 in step ST404 of FIG. 27 may be used as the display video signal. In this case, one parallax image 61L of the two parallax images 61L and 61R is displayed.

In ST413, the control portion 45 checks whether or not an operation input for terminating play of an image file has been performed in the operation portion 31. When the operation input for terminating play of the image file is performed, the play processing ends and the process proceeds to ST101 of FIG. 4. When an operation input for terminating play of an image file has not been performed in ST413, the process proceeds to ST414.

In ST414, the control portion 45 checks whether or not an operation input for starting measurement has been performed in the operation portion 31. When the operation input for starting the measurement is performed, the process proceeds to ST415. When the operation input for starting the measurement has not been performed, the process proceeds to ST413.

ST415 to ST424 show measurement processing in which image measurement is performed using the video signal stored in the image storage portion 42 in ST411. Hereinafter, an explanation will be made focusing on a different point from the measurement processing of ST110 to ST118 of FIG. 6.

In ST415, the video signal temporarily stored in the image storage portion 42 in ST411 is read as a display video signal and is output to the video signal processing portion 34 according to the control of the control portion 45. However, the measurement processing cannot be performed only with one parallax image of the two parallax images. Accordingly, in the case where the video signal temporarily stored in the image storage portion 42 is image data stored in the storage medium 44 in ST404 of FIG. 23, the measurement processing is not performed and the process proceeds to ST413 (not shown).

In ST416, the video signal processing portion 34 performs processing for dividing an image of the display video signal read from the image storage portion 42 into two parallax images and a video signal based on one parallax image (in this example, the parallax image 61L of FIG. 7) is output as the output video signal 101A to the signal conversion portion 38.

In ST417, similar to ST111, the video signal processing portion 34 performs processing for enlarging the one parallax image (parallax image 61L) of the two parallax images divided in ST416. A video signal based on the parallax image 61La after enlarging processing is output as the output video signal 101A to the signal conversion portion 38.

In ST418, the same processing as ST112 of FIG. 6 is performed. That is, the signal conversion portion 38 superimposes the measurement information 102, which is generated in the image measurement processing portion 43, on the output video signal 101A based on the parallax image 61La after enlarging processing and outputs it to the display portion 33 as the display video signal 101a. The display portion 33 displays the parallax image 61La on the basis of the display video signal 101a. The visibility for the examiner can be raised by displaying one of the two parallax images 61L and 61R. Although the parallax image 61L is used in this example, the parallax image 61R may also be used.

In ST419, the same processing as ST114 of FIG. 21 is performed. In ST420, the video signal temporarily stored in the image storage portion 42 in ST411 is read as a measurement video signal and is output to the image measurement processing portion 43 according to the control of the control portion 45. This video signal is the same as the output video signal 101A at the time of recording and is stored in the storage medium 44 as a measurement video signal in ST407 of FIG. 27.

In ST421 to ST423, the same processing as ST115 to ST117 of FIG. 6 is performed. That is, in ST422, the image measurement processing portion 43 performs measurement processing using still image data based on the measurement video signal read in ST420. Moreover, in ST423, the signal conversion portion 38 superimposes the measurement information 102, which is generated in the image measurement processing portion 43, on the output video signal 101A from the video signal processing portion 34 and outputs it to the display portion 33 as the display video signal 101a. The display portion 33 displays the parallax image 61L on the basis of the display video signal 101a. In ST424, the same processing as ST118 of FIG. 6 is performed.

As described above, according to the present invention, one parallax image can be displayed independently of other parallax images by processing a video signal such that image data including an image from any one optical system is extracted from image data including a plurality of images from a plurality of optical systems during a period (period including at least a point of time at which a measurement mode starts or a point of time at which a measurement result is generated by performing measurement) regarding measurement. Accordingly, since the visibility of a display image can be improved, it can be expected that the user would not be confused about performing an operation, such as input of a measuring point, on which parallax image.

In addition, since the display portion also becomes small as the endoscope apparatus becomes small and light, the displayed size of an image from each optical system may become small if image data including images from a plurality of optical systems is displayed simultaneously like the related art. As a result, the visibility of a display image may become worse. On the other hand, according to the present invention, the visibility of a display image can be improved by displaying one parallax image independently of other parallax images. For example, since one parallax image is enlarged and displayed by processing a video signal such that an image from one optical system is enlarged, the visibility of a display image can be further improved.

Moreover, although it may be difficult for the examiner to compare a plurality of parallax images visually and to check the matching degree since one parallax image is displayed independently of other parallax images, the examiner can check the matching degree by displaying the matching degree among a plurality of images corresponding to the measuring position.

While embodiments of the present invention have been described in detail with reference to the drawings, the specific configuration is not limited to the above-described embodiments but design changes and the like within the scope without departing from the subject matter of the present invention are also included.

According to the present invention, since an image from one optical system can be displayed independently of images from other optical systems by processing a video signal such that image data including the image from the one optical system is extracted from image data including a plurality of images from the plurality of optical systems during the period regarding measurement, the visibility of a display image can be improved.

What is claimed is:

1. An endoscope apparatus comprising:
    a video signal acquisition portion that images a test subject by a stereo optical system to acquire a video signal including right and left images which relate to the test subject;
    a video signal processing portion that processes the video signal to generate a display video signal;
    a measurement processing portion that performs measurement on the basis of the video signal; and
    a display portion that displays the display video signal, wherein:
        the video signal processing portion generates a first display video signal based on one, but not both, of the right and left images of the video signal by extracting one image from the video signal including the right and left images, and a second display video signal based on both the right and left images of the video signal;
        during a period regarding measurement, the display portion displays the first display video signal or the second display video signal along with at least one of operation-related information and measurement information; and
        a position where at least one of the operation-related information and the measurement information is displayed is controlled according to the first display video signal or the second display video signal displayed by the display portion.

2. The endoscope apparatus according to claim 1, wherein when the second display video signal is generated, the video signal processing portion processes the video signal such that the right image is displayed so as to overlap the left image.

3. The endoscope apparatus according to claim 1, wherein when the second display video signal is generated, the video signal processing portion processes the video signal such that the right image is displayed so as to overlap the left image, and the right image is enlarged.

4. The endoscope apparatus according to claim 1, wherein when the second display video signal is generated, the video signal processing portion processes the video signal such that the left image is displayed so as to overlap the right image.

5. The endoscope apparatus according to claim 1, wherein when the second display video signal is generated, the video signal processing portion processes the video signal such that the left image is displayed so as to overlap the right image, and the left image is enlarged.

6. The endoscope apparatus according to claim 1, wherein when the first display video signal is generated, the video signal processing portion processes the video signal such that the one image is enlarged.

7. The endoscope apparatus according to claim 6, wherein the video signal processing portion processes the video signal such that the entire one image is enlarged.

8. The endoscope apparatus according to claim 6, wherein the video signal processing portion processes the video signal such that a predetermined region of the one image is enlarged.

9. The endoscope apparatus according to claim 6, further comprising:
    a measuring position input portion that inputs a measuring position based on the first display video signal,
    wherein the measuring position input portion inputs the measuring position on the first display video signal enlarged by the video signal processing portion.

10. The endoscope apparatus according to claim 9, wherein the period regarding measurement includes a period for which the measuring position input portion inputs the measuring position.

11. The endoscope apparatus according to claim 10, wherein the measurement processing portion performs measurement on the basis of the video signal including the right and left images from the stereo optical system.

12. The endoscope apparatus according to claim 1, further comprising:
    a control portion that performs a control of storing the video signal including the right and left images from the stereo optical system in a storage medium.

13. The endoscope apparatus according to claim 12, wherein:
    the control portion reads the video signal stored in the storage medium and makes the video signal processing portion generate from the read video signal the first display video signal including the one image,
    the display portion displays the first display video signal, and
    the measurement processing portion performs measurement on the basis of the video signal stored in the storage medium.

14. The endoscope apparatus according to claim 1, wherein the measurement information includes at least one of information relating to the stereo optical system and information relating to a result of the measurement.

15. The endoscope apparatus according to claim 14, wherein the operation-related information includes information relating to a user-executable operation.

16. The endoscope apparatus according to claim 14, wherein the operation-related information includes a plurality of icons for performing user-executable operations.

17. The endoscope apparatus according to claim 1, wherein the operation-related information includes information relating to a user-executable operation.

18. The endoscope apparatus according to claim 1, wherein the operation-related information includes a plurality of icons for performing user-executable operations.

* * * * *